(12) United States Patent
Novosselov

(10) Patent No.: US 10,274,404 B1
(45) Date of Patent: Apr. 30, 2019

(54) PULSED JET SAMPLING OF PARTICLES AND VAPORS FROM SUBSTRATES

(71) Applicant: SpecTree LLC, Seattle, WA (US)

(72) Inventor: Igor V Novosselov, Seattle, WA (US)

(*) Notice: Subject to any disclaimer, the term of this patent is extended or adjusted under 35 U.S.C. 154(b) by 123 days.

(21) Appl. No.: 15/434,044

(22) Filed: Feb. 15, 2017

(51) Int. Cl.
| | |
|---|---|
| *G01N 1/24* | (2006.01) |
| *G01N 1/04* | (2006.01) |
| *G01B 11/24* | (2006.01) |
| *B05B 1/00* | (2006.01) |
| *B05B 1/04* | (2006.01) |
| *G01N 1/02* | (2006.01) |
| *H04N 7/18* | (2006.01) |

(52) U.S. Cl.
CPC ............... *G01N 1/24* (2013.01); *B05B 1/005* (2013.01); *B05B 1/044* (2013.01); *G01B 11/24* (2013.01); *G01N 1/04* (2013.01); *G01N 2001/022* (2013.01); *G01N 2001/028* (2013.01); *H04N 7/183* (2013.01)

(58) Field of Classification Search
CPC .......... G01N 2001/028; G01N 1/2214; G01N 2001/022; G01N 1/14; G01N 1/02; G01N 1/405; G01N 1/2211; G01N 33/227
See application file for complete search history.

(56) References Cited

U.S. PATENT DOCUMENTS

| | | | | |
|---|---|---|---|---|
| 3,748,905 A * | 7/1973 | Fletcher | ................... | G01N 1/02 73/28.04 |
| 3,970,428 A * | 7/1976 | Barringer | ............... | G01V 5/025 73/863.22 |
| 5,416,321 A * | 5/1995 | Sebastian | ................. | B25J 5/005 250/288 |
| 5,751,897 A * | 5/1998 | Van Alstyne | ............ | A62D 3/17 392/417 |
| 5,939,647 A * | 8/1999 | Chinn | ................... | G01N 1/2202 73/864.33 |
| 5,970,803 A * | 10/1999 | Staples | ................ | G01N 1/2214 73/23.41 |
| 6,269,703 B1 * | 8/2001 | Bowers | .................... | G01N 1/22 73/863.12 |
| 6,354,160 B1 * | 3/2002 | Staples | ................ | G01N 1/2214 73/863.12 |
| 6,378,385 B1 * | 4/2002 | Bowers | .................... | G01N 1/22 73/863.12 |

(Continued)

*Primary Examiner* — David A Rogers
(74) *Attorney, Agent, or Firm* — Kal K Lambert; Lambert Patent Services, LLC

(57) ABSTRACT

A non-contacting aerodynamic jet tool for collecting particles and vapors associated with surfaces. Opposing planar jets or planar jet arrays are used to liberate material from surfaces so that resuspended particulate matter and vapors can be collected for analysis. In operation, high-speed valves are triggered to create waveforms of high velocity pressurized planar jet bursts. The wall jets that traverse the surfaces exhibit unexpectedly high wall surface stress with velocity spikes characteristic of a chain of shock waves. Unlike axisymmetric jets, the wall jet tool flows over the target surface for a greater distance with wall shear stress having sufficient momentum to dislodge particles submerged in the boundary layer, dramatically improving sampling efficiency by lifting the particles and vapors from the boundary layer into a sampling intake for downstream analysis.

15 Claims, 24 Drawing Sheets

(56) References Cited

U.S. PATENT DOCUMENTS

Figure 1A:
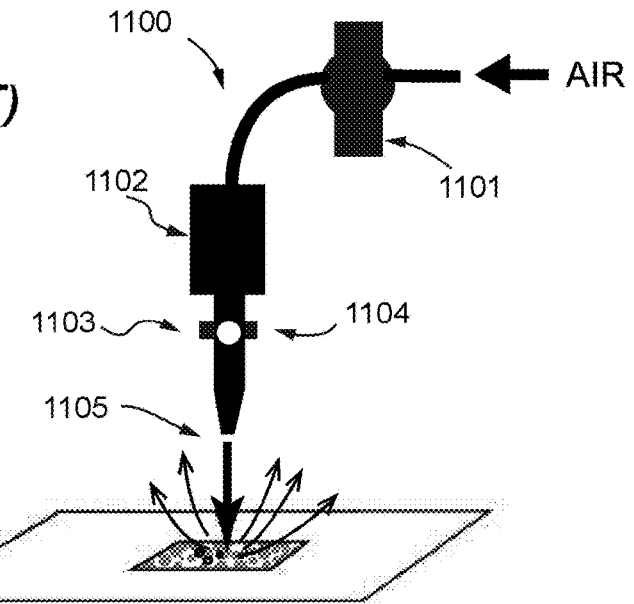

| Patent No. | | Date | Inventor | Classification |
|---|---|---|---|---|
| 6,449,035 | B1* | 9/2002 | Batchelder | G01N 1/02 356/237.1 |
| 6,828,795 | B2* | 12/2004 | Krasnobaev | G01N 27/622 324/464 |
| 6,861,646 | B2* | 3/2005 | Motchkine | G01N 1/02 250/281 |
| 6,888,128 | B2* | 5/2005 | Krasnobaev | G01N 1/02 250/281 |
| 6,895,804 | B2* | 5/2005 | Lovell | G01N 1/2202 73/31.05 |
| 7,098,672 | B2* | 8/2006 | Belyakov | G01N 1/22 324/451 |
| 7,100,461 | B2* | 9/2006 | Bradley | G01N 1/02 73/864.33 |
| 7,997,119 | B2* | 8/2011 | Wu | G01N 1/14 324/239 |
| 8,113,069 | B2* | 2/2012 | Settles | G01N 1/2226 73/863 |
| 8,122,756 | B2* | 2/2012 | Bunker | G01N 1/2202 239/7 |
| 8,307,723 | B2* | 11/2012 | Novosselov | G01N 1/2202 73/864 |
| 8,353,223 | B2* | 1/2013 | Bunker | B08B 7/0092 73/864.33 |
| 8,377,711 | B2* | 2/2013 | Henry | G01N 21/658 356/36 |
| 8,469,295 | B2* | 6/2013 | Bunker | G01N 1/02 239/551 |
| 8,561,486 | B2* | 10/2013 | Novosselov | B01D 15/08 73/864.32 |
| 8,592,758 | B1* | 11/2013 | Nilles | H01J 49/0431 250/288 |
| 8,626,467 | B2* | 1/2014 | Fang | G01N 1/2273 702/100 |
| 8,646,340 | B2* | 2/2014 | Zhang | G01N 1/24 73/863.11 |
| 8,665,433 | B2* | 3/2014 | Da Re | G01J 3/0237 356/301 |
| 8,756,975 | B2* | 6/2014 | Wu | G01N 1/14 73/31.05 |
| 9,048,076 | B2* | 6/2015 | Stott | H01J 49/0459 |
| 9,067,219 | B2* | 6/2015 | Bunker | G01N 1/02 |
| 9,134,205 | B2* | 9/2015 | Hillis | G01N 1/2202 |
| 9,335,236 | B2* | 5/2016 | Bry | G01N 1/2211 |
| 9,347,927 | B2* | 5/2016 | Wood | G01N 33/0009 |
| 9,390,899 | B2* | 7/2016 | Musselman | H01J 49/10 |
| 9,551,649 | B2* | 1/2017 | Houghton | G01N 33/227 |
| 2006/0249671 | A1* | 11/2006 | Karpetsky | G01N 27/624 250/288 |
| 2007/0158447 | A1* | 7/2007 | Bunker | G01N 1/02 239/1 |
| 2012/0044478 | A1* | 2/2012 | Da Re | G01J 3/0237 356/51 |
| 2012/0247230 | A1* | 10/2012 | McGill | G01N 21/71 73/863.11 |

\* cited by examiner

*FIG. 10B*
SLIT JET
101
SUCTION
INTAKE
BELL
99
*FIG. 10A*
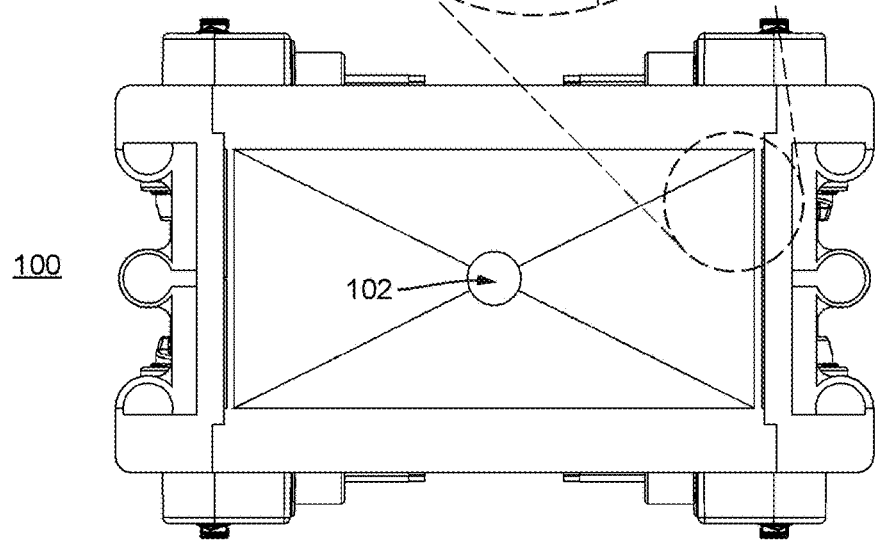
*FIG. 10C*
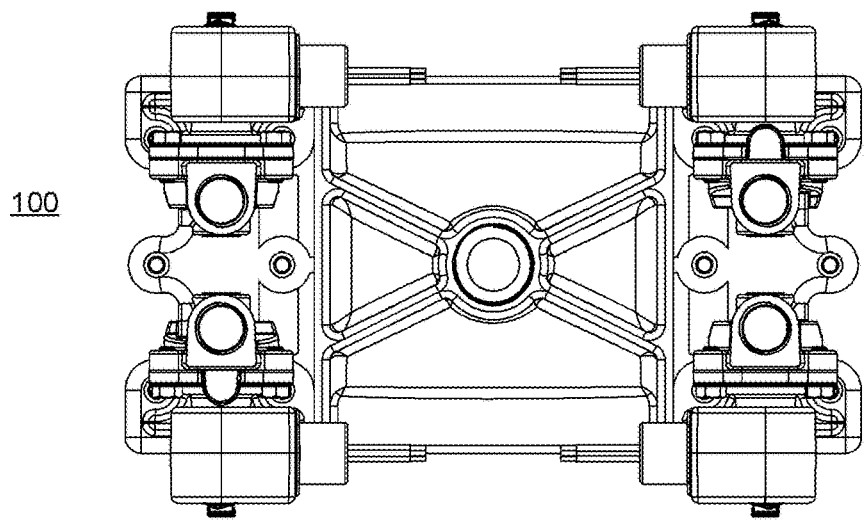

100

100

FIG. 23

METHOD

PROVIDING A SNIFFER BODY OF ANY ONE OF THE EMBODIMENTS OF THE INVENTION;

↓

PROVIDING A PRESSURIZED GAS SOURCE AND A SUCTION PRESSURE SOURCE;

↓

ACTUATING SUCTION PRESSURE AND PULSED FLOW OF PRESSURIZED GAS THROUGH THE SLOT JETS UNDER AUTOMATED CONTROL;

↓

DIRECTING OR STEERING THE ANGLED PLANAR JET BURSTS ONTO A SURFACE SO AS TO GENERATE OPPOSING WALL JETS;

↓

COLLECTING MOBILIZED PARTICLES, VAPORS AND BOUNDARY LAYER WHERE THE OPPOSING JETS COLLIDE AND LIFT UP;

↓

DIRECTING THE UPLIFT INTO A SUCTION INTAKE PORT FOR FURTHER PROCESSING.

PULSED JET SAMPLING OF PARTICLES AND VAPORS FROM SUBSTRATES

GOVERNMENT SUPPORT

This invention was made with partial government support under a subcontract to Contract No. W909MY-14-C-0020 awarded by the U.S. Army, Ft. Belvoir VA. The Government may have certain rights in the invention.

CROSS REFERENCE TO RELATED APPLICATIONS

This application is related to and claims priority to U.S. Provisional Patent Ser. No. 62/295,225 entitled "Jet Sampling of Particles and Vapors from Substrates" filed 15 Feb. 2016 which is herein incorporated in full by reference for all purposes.

FIELD OF THE INVENTION

The invention relates to sampling apparatus and to methods for analysis of trace analytes from surfaces and substrates. More particularly, the embodiments of the present invention relate to a high aspect ratio jet orifice or array for mobilizing particles and vapors at greater standoff distances.

BACKGROUND

Collection of "trace analytes" or "target analytes" may provide early warning of security risks or material information about environmental conditions generally. A preferred class of target analytes includes particulates and vapors, such as volatiles associated with explosives, where the volatiles are frequently found adsorbed on and associated with particles. As will be readily appreciated, particles adherent to substrates may be dislodged and aerosolized by application of high velocity jets to a substrate surface from a distance and are thus subject to analysis. The capacity to detect hazardous residues associated with particles on objects or vehicles, for example, and on persons with a history of having handled hazardous materials, is a rising security concern.

While it is known that an impinging directional jet may be used to dislodge and aerosolize particles and vapors from substrates, the jet action also scatters the particles, essentially diluting them in a larger sample volume and propelling them from the sampling area. While suction ports have been devised to collect larger sample volumes, the capacity to efficiently collect the dislodged material deteriorates rapidly with the distance of the suction port from the sample and the linear vector of the jet burst relative to the substrate or suction port. In short, some or all of the sample may be propelled away from the suction intake, leading to missed detection. While the behavior of the jet is reasonably predictable for a flat surface, when the surface is tilted away from the suction port or includes surface irregularities, significant sample loss occurs. This is particularly true for axisymmetric jets. Any increase in sample volume decreases sensitivity, and thus a satisfactory solution to this problem has not been demonstrated.

Related art is described for example in U.S. Pat. Nos. 5,491,337, 6,708,572 and 6,642,513. Various systems for hand search, gate security, walkthrough portals, and vehicle sampling have been advanced, and generally involve some kind of contacting sample collection such as a swab, or by concentration of very, very large volumes of air, such as from a portal or enclosure with a large fan-driven collection ductwork.

However, non-contact, open "sniffing" may be preferred, where air and particles associated with a suspect package or person are drawn into a nose-like detection system termed here a "non-contacting sampler". Early systems include those described in U.S. Pat. Nos. 5,491,337, 4,909,090, 7,275,453, 6,887,710, 7,942,033, 6,345,545, 7,299,711, 6,978,657, 6,604,406, 6,085,601, 5,854,431, RE38,797, 5,465,607, 4,987,767, 7,299,710, 8,307,723, 8,475,577 and in U.S. Pat. Publ. Nos. 20110186436 and 2012/0105839.

In preliminary work described in U.S. Pat. Publ. No. 20110186436 to Novosselov, continuous, non-contact sampling of trace materials from level surfaces was demonstrated for up to 6 inches distance using a circular jet array in which the jets define a "curtain wall" of moving air around a suction port, which is in turn surrounded by a secondary jet wall. For a given particle size, the drag force acting on the particle is related to the velocity of the wall jet at the location of the particle in relation to the jet impingement point. The higher the velocity of the wall jet at the particle location, the greater the lateral force for particle mobilization. But, performance limitations were reached. There are factors that limit the performance of the circular jet array sampler that cannot readily be overcome:

A) Limits on wall jet properties: The force applied to a particle on a surface greatly diminishes with an increase in the standoff distance H. With spaced axisymmetric jets, the jet spreads in all directions as a free jet and loses its momentum. Furthermore, after impingement on a solid surface, the wall jet velocity from the axisymmetric nozzle is rapidly diminished (due to momentum expansion) at shorter distances from the impingement point according to the $r^2$ law. The removal area (maximum wall shear stress location) for axisymmetric jet is relatively small and limits the interrogation zone of the circular array sampler. The force applied to the particle on a surface diminishes by a negative exponent of the standoff distance.

B) Geometric limits: Jets converge on a single point in the best designs, making collection of the mobilized sample impossible once the convergence distance is reached. Coherent jet momentum capable of imparting sufficient wall jet velocity has not proved possible at standoff distances greater than six inches for round nozzles because of parasitic losses in the free jet momentum. Circular jet geometry is more susceptible to the surface inclination and imperfections, as the individual jet timing and any sampler head misalignment will cause particle dispersion.

C) Limitations on independent jet function: Circular jet orifices were not readily controlled so as to vary timing and angulation. Pulse delay resulted in openings in the curtain wall through which particles were lost. Complex manifold geometry associated with circular jet arrays and uneven pressure distribution upstream of the nozzles results in the difficulties with controlling timing and dynamic pressure of each independent jet in the array to adjust for variations in stand-off distances, surface inclination and surface morphology.

In short, detection at a non-contact standoff of nine or twelve inches has not been possible using conventional technologies. The jet geometries developed to date are not robust and have not offered a solution to the problem of sampling from moving and complex surface geometries. Roadway detection of improvised explosive devices is needed, for example. The sampling problem is exacerbated where the substrate is an uneven surface, such as under a vehicle and the vehicle, with sampling apparatus attached, is in motion. Similarly, inspecting vehicles for concealed explosives is made difficult by the complex surfaces inside and on the underside of the vehicle.

A solution to these interrelated problems has not been achieved by trial and error or by computational fluid dynamics. Among other issues, special treatment for turbulence is required to obtain solutions. Even so, turbulence modeling techniques are not always consistent with the experimental data. Methods include Reynolds-averaged Navier-Stokes (RANS) models, Large Eddy Simulation (LES) and Detached Eddy Simulation (DES) are challenging due to prohibitively large grid requirement near the wall, especially for complex, real world sampling scenarios.

However, new computational approaches have been needed to speed directions useful in guiding experimental confirmation. To date, no fully operational trace analyte sampling and detection system for high throughput operation at larger standoff distances has been achieved. Any detection system is only as sensitive as the front-end sampling system. Thus, there is a need in the art, for a trace analyte surface sampling apparatus or system that overcomes the problems and limitations in the art, of which the above described literature is generally representative.

SUMMARY

The invention relates to aerodynamic sampling apparatus and to methods for sampling of trace analytes from surfaces and substrates. To understand the invention, it has to be first understood that the air (or "gas") in a representative inventive apparatus is not a "workpiece", it is part of the tool. The apparatus is configured to shape the flow of the gas from jet outlets to a suction inlet so that when impacted on a hand, artifact, or other solid surface, a wall jet (as will be defined below) is imparted with sufficient pressure and velocity so as to overcome drag forces on particles captive in a viscous "boundary layer" of stagnant air on the surface. Convergent planar jet bursts or arrays are used to mobilize material from surfaces at standoff distances less than the convergence point. Computerized systems for controlling the jet bursts may include sensor mapping for determining the proximity, angulation and fine structure of the substrate surface in three-dimensions. Individual jet bursts may be coordinated so as to direct samples to a suction port from an irregular surface.

The tool is configured for collecting analytes from a surface, the tool having at least one pair of planar jet orifices, each orifice having a supply of a pressurized gas, and each configured to discharge a planar aerodynamic jet, such that the jets converge at a convergence distance from the orifices. On striking a solid target surface at a standoff distance less that the convergence distance, the jets are deflected as opposing wall jets configured so that the opposing wall jets collide on a solid target surface and lift up therefrom any mobilized particles or vapors into a sample intake port disposed between the pair of planar jet orifices. In one instance the planar aerodynamic jets are supersonic and surprisingly, the wall jets also comprise at least one shock front, more preferably a train of shock fronts.

The flow of gas jets in a supersonic regime, for example, may be used to achieve sampling of particles and vapors from that surface at "standoff" distances of more than 6 or 9 inches, and even at 12 inches. At closer distances, with low outlet pressures that are readily achievable with portable equipment, wall shear force can be achieved that is sufficient to mobilize particles as small as 1 or 100 micrometers in aerodynamic height. These jets are generally slit jets or have an aspect ratio ($A_L$) of length to width of the resultant jet flow such that $A_L$ is greater than 5, more preferably greater than 10, such that as the planar sheet of jet-velocity air impacts a surface at an angle, deflection of the jet results in translation of the jet into a linear shock wave moving coherently and essentially parallel to the surface (i.e., a "wall shear jet"), even when the flow of gas originates from more than 12 inches away, an advance in the art. The increase in working distance is dependent on the shaping and control of jet geometry and coherence, and by opposing wall shear jets having sufficient wall shear velocity and pressure, efficient collection of microparticles and vapors is achieved.

The apparatus finds use in active surveillance, such as for detecting explosives in aerosols, chemical residues or "trace analytes", including those on persons, vehicles, buildings or luggage. Continuous, semi-continuous, or batch mode operation is enabled according to the requirements of the downstream analytical unit and the needed threshold for detection. "Trace analytes" may take the form of a particulate composed of a target constituent or constituents, a free vapor composed of a target constituent or constituents, or a particulate combined with a vapor. The invention relates particularly to such apparatus and methods as are useful in non-contacting sampling and detection of trace analyte residues on irregular, angular, and complex surfaces.

A representative apparatus for collecting an aerosolized sample of particles and vapors from a target surface according to the invention comprises an apparatus having i) a suction intake portal; ii) a pair of slit jet nozzles or a plurality of slit jet nozzles in an array disposed on either side of the intake, the jet nozzles each having a valved fluid connection to a pressurized air supply, and iii) a high-speed controller for actuating the jet nozzles in a pulsatile pattern of bursts according to a computer-generated actuation waveform or user input. Downstream detection of target analytes may involve sample concentration and analysis by methods known in the art.

A representative apparatus for for aerodynamic mobilization and capture of particles and vapors at a non-contacting standoff distance from a target surface includes a sampler body, the sampler body having a) an array of two or more slit jet orifices on a first surface of the body, each with a fluidly connected gas pressure source; b) a sampling intake port disposed between the two or more slit jet orifices; c) wherein the slit jet orifices are fluidly connected to a pressure source and are arrayed in pairs, each the pair having a first slit jet orifice configured to discharge a first planar jet and a second slit jet orifice configured to discharge a second planar jet toward a target surface without contact of the sampler body on the target surface; and, d) wherein each the pair of slit jet orifices are angled to generate opposing wall jets, the wall jets having a velocity effective to liberate and lift particles and vapors from a target surface and direct the flow up towards the sampling intake port.

In a first embodiment, the apparatus includes a valve or valves configured to generate planar jet bursts from each of the planar jet orifices according to a computer-controlled timing waveform. The slit jet orifices may be valvedly controlled as a group or groups or may be operated individually, and may be synchronous or asynchronous. In another embodiment, the apparatus is configured to supply a continuous flow of a pressurized gas from each the planar jet orifices.

In a preferred embodiment, the sampling intake port may be fluidly connected to a suction pressure source so that particles and vapors are drawn through the sampling intake port, or the device may rely on the uplift of the jets alone to drive particles and vapors into the sampling inlet port.

In some embodiments, an array of two or more slit jet orifices is operable in sampling particles and vapors over a standoff distance from 1 cm to 30 cm or more. In other embodiments, the array is operable in sampling particles and vapors over a standoff distance from 30 cm to 1 meter or more.

Slit jet orifices may be operable in sampling particles and vapors at jet pressures of less than 100 psig, more preferably pressures of less than 60 psig, and most preferably at pressures less than 30 psig. Lower pressure is particularly preferred for portable applications in which the sampling apparatus is operated without external connections.

Also disclosed is a non-contacting sampler apparatus mounted on a robotic arm, in which the robotic arm is enabled to move the sampler body in more than one degree of freedom (X, Y, Z and rotationally) according to the three-dimensional map of the target surface. The sensor may be a camera having circuitry enabled to provide a remote display of a video feed from the camera. In other instances the sensor may be a particle sensor, and the apparatus may be operated in a feedback loop condition to optimize particle collection.

In a preferred apparatus, at least one sensor is configured to supply range-finding data to a computational module with processor, wherein the processor is supplied with memory and an instruction set for calculating a map of a target surface, the map including a distance between each of the jet nozzles and the substrate at a designated map point below the suction intake portal. Also conceived is an actuation module in digital communication with the computational module, in which the actuation module configured to control the analog operation of the valved fluid connections. In alternate embodiments, each jet burst is targeted to an individual designated map point and is defined by an exit velocity, and is angulated such that a jet burst emitted therefrom is angled to intersect the designated map point for each the jet, thereby being deflected with a surface-reactive momentum. The computational module is configured to valvedly emit a first jet burst from a first jet nozzle such that a first-striking jet burst impacting its dedicated map point is angled in its surface-reactive momentum by a second striking jet burst from a second jet nozzle impacting a proximate designated map point from an opposing angle after a delay such that particles and vapors entrained in the first-striking jet burst are propelled upward toward the suction intake port rather than outward away according to the surface-reactive momentum of the first-striking jet plume. The computational module operates the actuation module to effect a first strike of a jet burst on a first side of a map point at a theta angle and a second strike of a jet burst on a second side of a proximate map point at a negative theta angle, such that as the jet bursts meet, the jet surface-reactive momentum converges and is redirected upward. Surface-reactive momentum is essentially deflection caused by the vector of the jet being redirected according to the tilt or any obstructions in the substrate surface. The vectors of the opposing jets results in uplift at the convergence point. Pulse duration, pulse frequency, and the timing of the jets may be finely calculated to allow for differences in surface contour between the two points on the surface at which the jets strike. Essentially, the jets converge, with a slight delay, forming a "pocket" in which the first and second air masses rise up and are directed to the suction port so that it can be captured by aspiration. In some instances the coherence of the uplift obviates the need for a suction pressure at the sampling inlet.

As currently practiced, the jet nozzles are slit jet apertures and are disposed in parallel configuration contralaterally across the suction intake port; however, round nozzles in regular linear arrays may also be used. Time delay is used to coordinate jet bursts so as to effect a sweeping and lifting action on particles and vapors dislodged from a substrate surface.

Any ambient crosswind can also be calculated when designing a jet sequence. Similarly, vehicle motion, such as vehicles driving on a road, can also be factored in to the calculations. Because of drag characteristic of air masses in motion, care must be taken, however, not to exceed the capacity of the jet "pocket" to entrain the desired air samples. Most preferred are parallel slit apertures as currently practiced, but the slit apertures may be angulated slits and arrays of slits. The apparatus may also include one or more directional jet nozzles having active control of angulation.

In one embodiment, the computational module controls the actuation module to emit a continuous series of paired jet bursts, wherein the first striking jet burst and the second-striking jet burst are offset by a time delay. Jet pressure, pulse duration and standoff distance can be varied to achieve desired operating conditions of the sampler. In alternative embodiments, the computational module controls the actuation module to emit a continuous series of paired pulses, wherein the first striking jet burst and the second-striking jet burst are distinguished by relative velocity or duration. In yet other embodiments, the computational module controls the actuation module to emit a continuous series of paired pulses, wherein the first striking jet burst and the second-striking jet burst are differentiated by an angular compensation.

With respect to a mapping sensor, generally a laser rangefinder is used. Lasers can rapidly scan an area and produce a distance model of a complex contoured surface. Infrared laser rangefinders are preferred because of their partial resistance to dust. In other embodiments, a robotic arm can be used to adjust non-contacting sampler head position and angulation based on the mapped surface geometry, standoff distance, and the desired jet parameters for the best sample resuspension and capture scenario. In an embodiment for surveying surfaces while the detector apparatus is in motion, the body includes sets of arrays of slit jets, each array acting in series to sweep a sample into the suction intake port. In one configuration, two slit jet apertures act essentially as a "Vee" shape, where the "Vee" points opposite the direction of overall motion of the detector, as for example a vehicle moving along a road surface. As soon as opposing slit jets have dislodged a sample, a third jet, for example an arcuate jet, traps the material in the pocket, and by maintaining thrust from the two "Vee" jets, causes the momentum of the vehicle to "scoop" the material into the suction intake port. Conceptually, the "pocket" resembles a trapped eddy, and efforts to model the residence time of foreign particles and vapor mathematically suggest improved residence time as is needed to increase the efficiency of the suction operation. Multiple slit jets may be used simultaneously to cover larger surfaces side to side.

The invention also includes methods of operation of jet assemblies, methods of surveillance, methods for use on moving vehicles, and methods which include miniaturization of components for screening of persons and interior of vehicles or luggage, for example. In combination with sample concentration and analytical modules, fully operational portable and stationary jet-assisted non-contacting sampler head assemblies are operative having extended standoff sampling distances.

Figure 18:
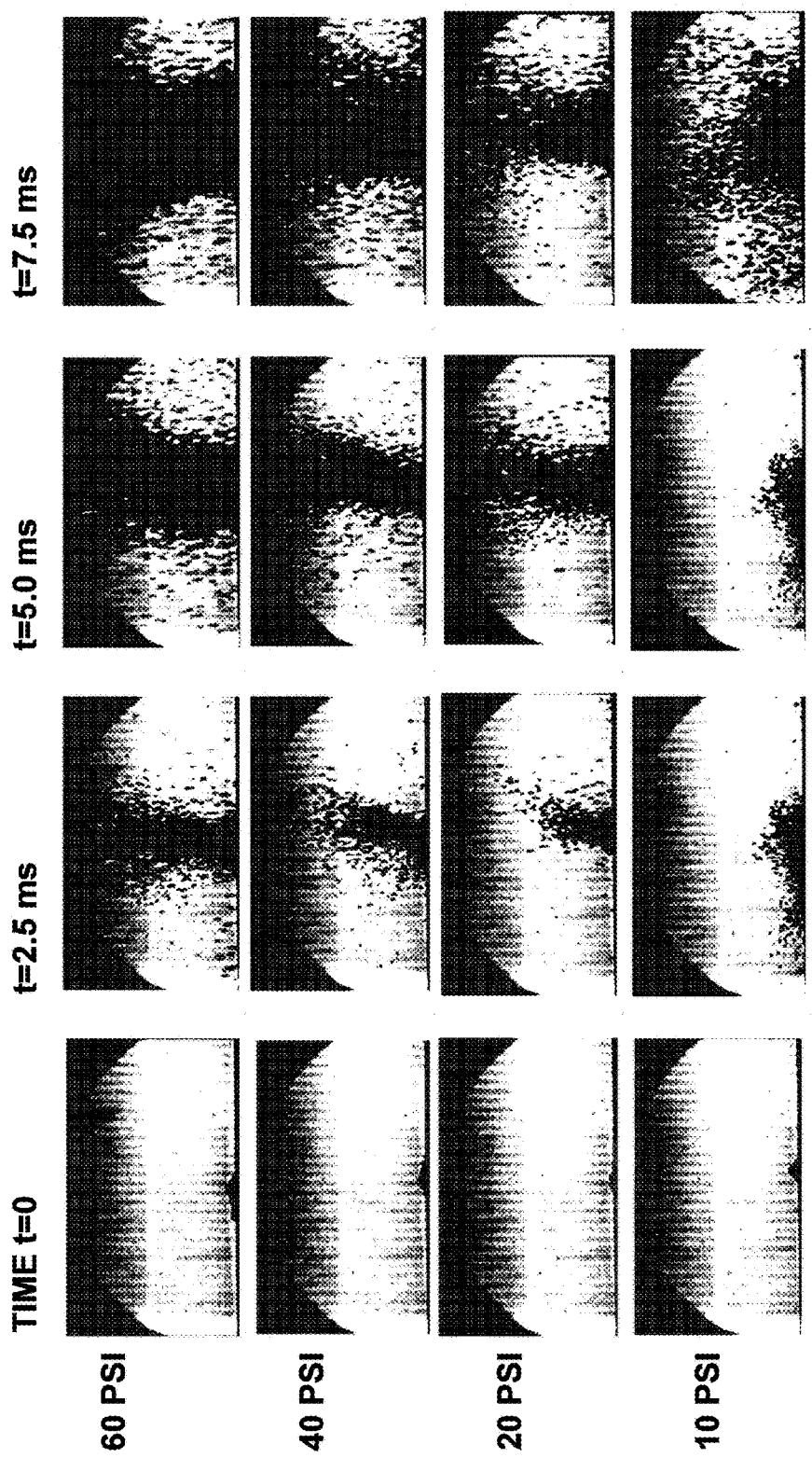

The elements, features, steps, and advantages of the invention will be more readily understood upon consideration of the following detailed description of the invention, taken in conjunction with the accompanying drawings, in which presently preferred embodiments of the invention are illustrated by way of example.

It is to be expressly understood, however, that the drawings are for illustration and description only and are not intended as a definition of the limits of the invention. The various elements, features, steps, and combinations thereof that characterize aspects of the invention are pointed out with particularity in the claims annexed to and forming part of this disclosure. The invention does not necessarily reside in any one of these aspects taken alone, but rather in the invention taken as a whole.

BRIEF DESCRIPTION OF THE DRAWINGS

The teachings of the present invention are more readily understood by considering the drawings, in which:

FIG. 1A is a view of a conventional axisymmetric jet for particle sampling from surfaces. The figure is adapted from a published work [Keedy et al., Removal Rates of Explosive Particles From a Surface by Impingement of a Gas Jet. Aerosol Sci Tech. DOI 10.1080/02786826.2011.616920.]

FIG. 1B is a cross-section through a representative conventional axisymmetric jet nozzle, with jet shape and structure illustrated schematically.

FIG. 2 summarizes key parameters that characterize the tool (i.e., gas flow) as used to improve particle mobilization and capture from a surface. Particle mobilization is in part a function of wall jet velocity and shear stress in the viscous boundary layer.

FIG. 3A is a CAD view in open section of a "non-contacting sampler head assembly" having a pair of slit apertures, one on each of the sides of a central suction intake. The phantom lines indicate that the slit geometry may be extended laterally to increase the aspect ratio of each jet slit nozzle.

FIG. 3B is a schematic showing the operation of a non-contacting sampler nose with valves for delivering pulsatile jet bursts FIGS. 3C, 3D and 3E are representative sections of a non-contacting sampler head assembly with jet outlets and sampling intake. Sections are taken from top to bottom as shown in FIG. 3B.

FIG. 4 is a Schlieren image of two convergent jets emitted from representative slit jet apertures of the invention and impinging on a solid surface. Visible between the impinging jet cores are lateral wall jets colliding and lifting up as a turbulent air mass directed into a suction intake in the center between the jet cores.

FIG. 5A is a block diagram of a "smart jet" apparatus configured to use sensor data to map a substrate surface and to coordinate activation of opposing slit jets so as to optimize sample entrainment in a suction port. FIG. 5B is a schematic view in close-up, showing asynchronous jet burst activation and control of angulation on a sloped surface.

FIG. 6 is a plot showing actuation of two pairs of jet bursts from opposing slit jets. The timing, duration, angulation and amplitude of jet bursts may be calculated to optimize asynchronous valve actuation for collecting a sample. Feedback sensor loops may also be employed.

FIG. 7 is a schematic view of a more complex slit jet apparatus with contralaterally disposed mapping sensors, a range mapping module, and analysis module in a single package.

FIG. 8 is a representation of dual jets, their angulation, and the standoff distance to sample versus convergence distance. A spread of 4 inches in breadth of sampling area is achieved in this example, in which the standoff distance is 12 inches.

FIGS. 9A and 9B are perspective views of a quadruplex jet array having two slit jets around a central suction intake. In the first view, the large suction intake of the non-contacting sampler head assembly is visible as sloping planes. In the second view, the common port of the suction inlet is visible (without connection) and four high speed valves are mounted, one above each of the jet apertures. Bundles of wires to a controller are also represented without connections.

FIGS. 10A and 10C are isometric views of the underside and the top of the quadruplex jet array and non-contacting sampler head assembly of the preceding figure. The aspect ratio of each jet is very high at the aperture as demonstrated in detail view FIG. 10B (circled and magnified). Each jet extends along the contralateral edges of the central suction intake.

FIGS. 11A and 11B set up a series of section planes, beginning with the long axis center sectional view of FIG. 11B. Here the jet aperture size is exaggerated for clarity but the convergent angulation and proximity to the center suction intake are depicted.

FIGS. 12A and 12B are sections taken through the non-contacting sampler head assembly. In the first view, the cut plane is perpendicular to the long axis section depicted in FIG. 11B. In FIG. 12B, the cut plane goes through the valve tree (details not shown), the ductwork to the jet manifolds, and cuts the pair of jet apertures at the base of the structure so as to illustrate the aspect ratio of the jet length versus width, referencing FIG. 10B.

FIGS. 13A and 13B are side and end views of the non-contacting sampler head assembly represented in FIGS. 9A through 13B.

FIG. 14 is an exploded view showing how a non-contacting sampler head with high aspect ratio jet aperture is assembled. The valve trees are not shown for clarity.

FIGS. 15A and 15B are Schlieren images of jet substructure. A comparison is shown between a slit jet of the inventive non-contacting sampler head and a conventional nozzle jet. Plate shock occurs with both jets, but the slit jet is characterized by a shock train in the wall jet. This behavior is amplified when the slit jet is angled from vertical.

FIGS. 16A and 16B are computational fluid dynamics simulations of opposing slit jets. essentially the same setup as depicted figuratively in FIG. 8. Two views are shown, one at lower pressure and one at higher pressure. A central suction inlet draws the jets into a particle and vapor collector.

FIGS. 17A and 17B are plots of wall shear stress (τ, Pa) at four different normalized pressure ratios. The top plot shows the data for a slit jet; the bottom plot shows qualitatively different data for a round nozzle jet. Surprisingly, with slit jets, wall pressure has a surprising "reach", here extending over 50 mm at substantial shear wall stress (~200 Pa) versus essentially zero with an axisymmetric jet configuration. Distance from impingement point is evaluated, showing a dramatically improved profile with the slit jet pair.

FIG. 18 is a montage of photographs taken with a high speed camera. The experimental results speak for themselves.

Figure 19A:
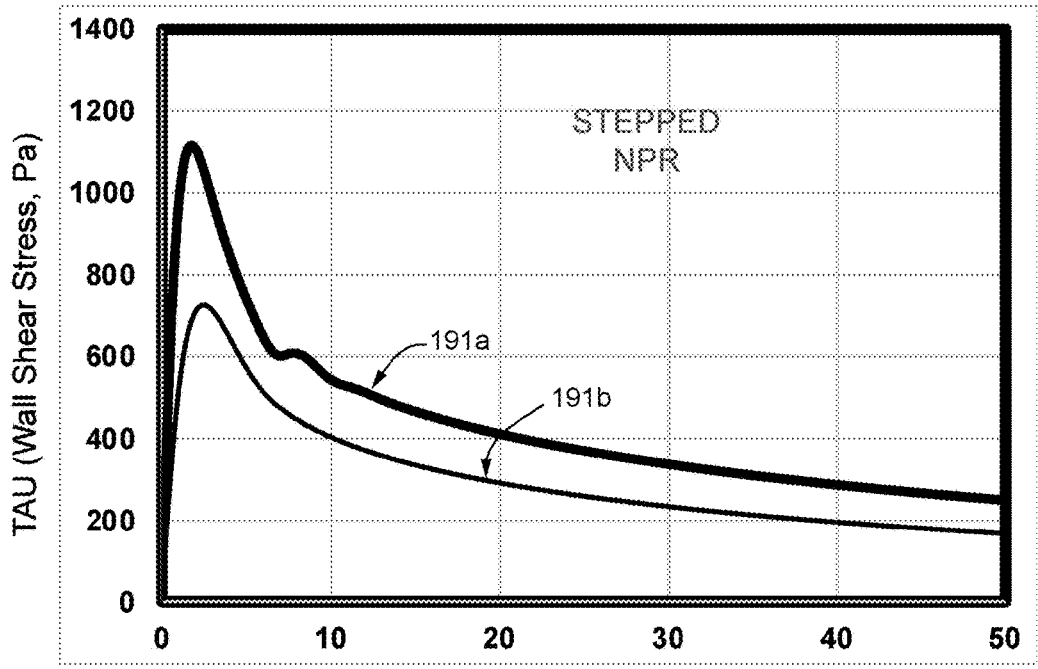
Figure 19B:
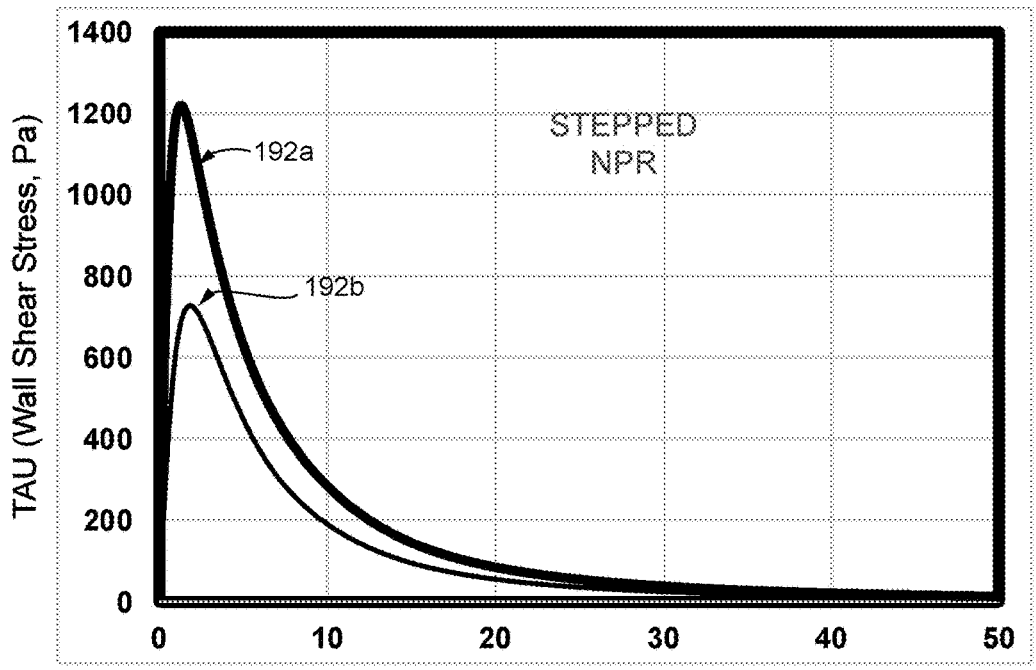

FIGS. 19A and 19B are plots of wall shear stress (τ, Pa) at higher normalized pressure ratios to demonstrate that increased jet pressure does not remedy the deficit in reach of the wall jet for axisymmetric jets. This is true even though the peak wall shear is slightly higher for the axisymmetric jet very close to the impingement point. Outside that zone, jet force drops rapidly according to the r-squared law.

FIGS. 20A, 20B, 20C, and 20D are schematics of other slit jet arrays operative according to the invention in enabling increased particle recovery at much longer standoff distances. The drawings are not to scale.

FIG. 21 is a perspective view of an apparatus combining an array of two rows of tubular jet nozzles on either side of a central suction port. Jet flow is additive in overlaps and the array is thought to behave somewhat like a slit jet because of the high aspect ratio of the combined array impingement zone.

FIGS. 22A and 22B suggest that linear and segmented jet arrays having an extended aspect ratio (>3) also achieve a higher capture efficiency at greater standoff distances.

FIG. 23 is a representative model of a process for operating a slit jet array of the invention.

The drawing figures are not necessarily to scale. Certain features or components herein may be shown in somewhat schematic form and some details of conventional elements may not be shown in the interest of clarity, explanation, and conciseness. The drawing figures are hereby made part of the specification, written description and teachings disclosed herein.

Glossary

Certain terms are used throughout the following description to refer to particular features, steps or components, and are used as terms of description and not of limitation. As one skilled in the art will appreciate, different persons may refer to the same feature, step or component by different names.

Components, steps or features that differ in name but not in structure, function or action are considered equivalent and not distinguishable, and may be substituted herein without departure from the invention. Certain meanings are defined here as intended by the inventors, i.e., they are intrinsic meanings. Other words and phrases used herein take their meaning as consistent with usage as would be apparent to one skilled in the relevant arts. The following definitions supplement those set forth elsewhere in this specification.

Unless otherwise defined, all technical and scientific terms used herein have the same meaning as commonly understood by one of ordinary skill in the art to which this invention belongs. In case of conflict, the present specification, including definitions, will control.

"Wall shear stress": is defined as $$\tau = \mu \frac{dv_x}{dy}$$

where τ is the shear stress, μ is density, and $dv_x/dy$ is the "X" velocity gradient in the "Y" direction (also sometimes written δu/δy). "Tau" (τ) has units of Pascals, mu (μ) is the fluid molecular viscosity.

For a free supersonic jet, three distinct regions can be observed: (1) the under-expanded region where the flow is supersonic, Ma≥1; (2) the compressible flow region, 0.3>Ma>1.0; and (3) a subsonic jet, Ma<0.3.

With reference to jets impinging on surfaces, an impinging jet typically is analyzed as having three regions of flow: a free jet that may contain shock structures, a stagnation region where the moving fluid impinges on a solid surface, and a wall jet that is diverted to run along the surface of the plate.

Supersonic flow regime: gaseous flows having velocities of 1.0 Mach or greater in at least a part of the flow profile. The supersonic jet is associated with rapid changes in fluid density (shock and expansion waves). With reference to jets impinging on surfaces, a supersonic impinging jet typically is analyzed as having three regions of flow, a free jet that may contain shock structures, a stagnation region where the moving fluid impacts a solid plate, and a wall jet that is redirected along the surface of the plate.

Compressible flow regime: a gaseous fluid having regions of velocities in the range of Mach 0.3 to <1.0. Compressible flow of a gas stream is characterized by changes in density with respect to pressure along a streamline.

Incompressible flow regime: a gaseous fluid having a velocity where the Mach number does not exceeds about 0.3, although the transition from incompressible to compressible is not a precise demarcation, and mixed flow regimes may occur.

Critical Dimension—the dimension $L_c$ in a channel or tube that is a determinate in establishing flow velocity and flow regime conditions of a gas stream through a channel or tube, and used here to indicate the width of a slit jet for calculation of H/D. The critical dimension also determines the local Reynold's number Re and is used in calculation of the Stokes Number Stk and the choke pressure "Analysis and concentration modules" are known in the art for concentration, detection and identification of particles or vapors in aerosols and may be selected for physical, chemical or biological analysis for combination with the front end sampler, the "non-contacting sampler" of the invention.

Detection methods include visual detection, machine detection, manual detection or automated detection. Means for detecting include laser particle scattering, liquid chromatography (LC), high pressure liquid chromatography (HPLC), high pressure liquid chromatography with mass spectroscopy (HPLC/MS), gas chromatographic mass spectroscopy (GC/MS), gas chromatography coupled to electro-capture detection (GC-ECD), atmospheric pressure ionization time-of-flight mass spectrometry (TOFMS), ICP-mass spectrometry, ion mobility spectroscopy (IMS), differential ion mobility spectroscopy, secondary electrospray ionization—ion mobility spectrometry, electrochemistry, polarography, electrochemical impedance spectroscopy (EIS), surface plasmon resonance (SPR), fast atom bombardment spectroscopy (FABS), matrix-assisted laser desorption ionization mass spectrometry (MALDI/MS), inductively coupled plasma mass spectroscopy (ICP/MS), Raman spectroscopy (RS), FTIR, SAW spectroscopy, surface-enhanced Raman spectroscopy (SERS), laser induced breakdown spectroscopy (LIBS), spark-induced breakdown spectroscopy (SIBS), lateral flow chromatography, NMR, QR (quadrupole resonance), and so forth. Detection systems are optionally qualitative, quantitative or semi-quantitative. Of particular interest for detection of explosives are electron capture (often combined with gas chromatography), ion mobility spectroscopy, mass spectroscopy, and chemiluminescence (often combined with gas chromatography).

One common analytical instrument for detection of nitrate-type explosives relies on pyrolysis followed by redox (electron capture) detection of NO2 groups (Scientrex EVD 3000), but is prone to false alarms. So too is chemiluminescence. Also of interest is differential mobility spectroscopy as described in U.S. Pat. No. 7,605,367 to Miller. Ion mobility spectroscopic (IMS) detectors are in widespread use and typically have microgram or picogram sensitivity. IMS requires ionization of the sample, which is typically accomplished by a radioactive source such as Nickel-63 or Americium-241. This technology is found in most commercially available explosive detectors like the GE VaporTracer (GESecurity, Bradenton, Fla.), Sabre 4000 (Smiths Detection, Herts, UK), Barringer IonScan™ 400, and Russian built models.

The luminescence of certain compounds undergoing reaction with electron-rich explosive vapors has been improved with the introduction of amplifying fluorescent polymers as described in U.S. Pat. No. 7,208,122 to Swager (ICx Technologies, Arlington Va.). Typically, vapors are introduced into a tubular sensor lined with a conductive quenchable fluorescent polymer by suction. These sensors lack a preconcentrator and work only for analytes with electron-donating properties. More recent advances have extended work with fluorescent polymers to include boronic peroxide-induced fluorescence, as is useful for detecting certain classes of explosives.

FIDO® detects TNT and other explosives (J. S. Yang, and T. M. Swager, 1998. "Porous Shape Persistent Fluorescent Polymer Films: An Approach to TNT Sensory Materials." Journal of the American Chemical Society, 120, 5321-5322). It is approximately 1000 times more sensitive than most explosive detection systems currently used for passenger screening in airports. This sensitivity is achieved by using cooperatively fluorescent polymeric materials. In the absence of TNT, the polymers fluoresce (emit visible light) when exposed to light of the correct wavelength. When molecules of TNT are present, the intensity (brightness) of the fluorescence is quenched by a self-amplifying effect, and a sensitive photo detector then detects the drop in fluorescence intensity. At this time, the sensor detects TNT, 2- and 4-DNT, and other nitro aromatic compounds derived from TNT. In laboratory tests, the sensor has demonstrated lower limits of detection of one femtogram (1×10-15 grams) of TNT vapor. Fluorophore polymers for detecting other hazardous or illicit materials may also be used. Publications related to coordinately quenched fluorophores for trace analyte detection are incorporated in full by reference.

A MEMs-based pre-concentrator (an adsorbent bed) has recently been integrated into the FIDO explosives vapor detector to increase the volumetric sampling rate of the system. This adsorbent matrix increased the volumetric sampling rate of fluorescence detection systems from 30 mL/min to in excess of 2 L/min by a modified batch process with thermal cycling of the adsorbent matrix. Adsorbent matrices are well known in the art, having been pioneered by Almirall. Recent work includes U.S. Pat. Nos. 6,171,378 and 7,118,712 to Manginell and U.S. Pat. No. 7,713,421 to Galbraith, WIPO Doc. No. 2010/095123 to Langford and in US Pat. Appl. Doc. 2009/008421 to Almirall, for example. Literature on selection and use of sorbent materials for SPME and related preconcentration arts is widely available. A more detailed reading list includes E. J. Houser et al, 1999, Sorbent coatings for detection of explosives vapors: applications with chemical sensors, Proceedings of the SPIE, Orlando, Fla., 3710:394-401; Houser, E J et al, 1994, Linear and Hyperbranched Hydrogen Bond Acidic Poly(silylene methylene)s for Chemical Sensor Applications, PMSE Preprints 203, 88, 548, in R. A. McGill, M. H. Abraham, J. W. Grate, Choosing polymer coatings for chemical sensors," CHEMTECH 24, pp. 27-37; Houser E J et al. 2001. Rational materials design of sorbent coatings for explosives: applications with chemical sensors, Talanta 54:469-84; Pai R S et al, 2008, Sorbent Coatings and Processing Techniques for Trace Analysis of Hazardous Materials in Micro/Nano Sensors, IEEE University/Government/Industry Micro/Nano Symposium, 2008. UGIM 17th Biennial Volume, Issue 13-16:153-156; Voiculescu, I et al, 2006, Micropreconcentrator for Enhanced Trace Detection of Explosives and Chemical Agents, Sensors Journal, IEEE, Volume 6:1094-1104; U.S. Pat. No. 6,660,230; US Pat. Appl. Nos. 2005/0276726 and 2009/0084201, all of which are incorporated herein in full by reference.

Other analytical modalities are known in the art, and include the MDS Sciex CONDOR, Thermedics EGIS, Ion Track Instruments Model 97, the Sandia Microhound, Smith's Detection Cyranose, FIDO® (FLIR Systems, Arlington Va., formerly ICx Technologies), Gelperin's e-nose (U.S. Pat. No. 5,675,070), Implant Sciences' Quantum Sniffer', and others. However, these technologies are associated with aspiration and analysis of free vapors without concentration, which are typically in vanishingly small concentrations, either because a) the vapor pressure of the material is inherently small, or b) if vapor pressure is larger, then significant quantities of a more volatile analyte will have been lost due to ageing of the material prior to sampling. Also a detriment, some of these detectors have had maintenance issues related to fouling or poisoning of the adsorbent or detector due to aspiration of particles. Thus the system of the invention offers a clearcut advance in the art, permitting the separation of vapors from a moving gas stream without filtration or adsorption onto a solid phase bed and thus permitting continuous analysis when coupled to a suitable detection platform. Semi-continuous and batch type processes are also flexibly accommodated by hot trapped vortex vapor concentrators. Publications related to these processes are incorporated in full by reference.

Conventional systems are described in U.S. Pat. Nos. 7,256,396, 7,260,483, and 6,972,408 and more recently in US Pat. 2010/0252731, where high vacuum is used (0.1 to 30 mTorr). Also of interest is the Aerodyne Aerosol Mass Spectrometer [Takegawa et al, 2005, "Characterization of an Aerodyne Aerosol Mass Spectrometer" Aerosol Sci Tech 39:760-770; Bae et al, 2007, "Interference of organic signals in highly time resolved nitrate measurements by low mass resolution aerosol mass spectrometry. J Geophys Res 112: 1-16]. In this system, analyte vapors are released by laser ablation from a very well collimated particle beam (typically <0.25 mm diameter) and ionized in flight. The resulting vapors are conveyed in a buffer gas at high vacuum, typically with Einzel lensing, into a mass spectrometer. However, the detector can be badly damaged by the entry of intact particles that escape the laser. Moreover, the particle-by-particle approach and requirement for high vacuum substantially limits application for high throughput analysis. Publications related to these processes are incorporated in full by reference.

Related systems are described in PCT Publication WO/2008/049038 to Prather, U.S. Pat. No. 6,906,322 to Berggren, and U.S. Pat. No. 6,664,550 to Rader. These devices are readily overloaded when confronted with large amounts of complex mixtures, interferents, and dust, such as are likely to be encountered in routine use and hence have had limited applicability. Publications related to these processes are incorporated in full by reference. Like FIDO, mass spectroscopy also offers the potential for miniaturized continuous flow detection and likely will continue to have an inherent capacity to simultaneously detect a broader range of possible target analytes. Conventionally, the inlet flow rate into an MS instrument is small (less than 1 mL/min). A common practice employed with detectors that can process limited sample volumes is to use a split flow into the detector that essentially purges most of the sample; this approach is undesirable since most of the sample volume is not analyzed.

Alternatively, an adsorbent matrix like that described above may be used to pre-concentrate a trace vapor stream, with intermittent thermal cycling to release the adsorbed vapors. The adsorbent bed can be heated to desorption in approximately 100 ms, and because it has low thermal mass the chip cools back to ambient temperature in less than 5 s when a flow of air is drawn through the chip. Hence, the sampling duty cycle of the chip would be on the order of 8-10 s/cycle, which is compatible with a batch-sampling approach.

Very recently, exceptionally compact mass spectrometers utilizing cylindrical ion trap (CIT) technology have been developed at Purdue University and are being commercialized by ICx Technologies. This is a significant advancement in MS capability because it allows for continuous flow under conditions where ions are collected in an electrical field and may be released into the detector according to their mass/charge ratio without need for a chromatographic step. Complex target analyte fingerprints can be accumulated and matched with libraries of known substances. Like traditional quadrupole ion traps with hyperbolic electrode geometries, the CIT utilizes a three-electrode structure comprising a ring and two end-cap electrodes to perform mass analysis. Ions generated in the manner described above are trapped between the electrodes by an oscillating electric field. Ions of a particular mass-to-charge ratio can be trapped within this field for an indefinite amount of time and may be released for analysis according to programmed instructions. Publications related to CIT are incorporated in full by reference. Once ions are trapped in the CIT, they can be further manipulated for MS/MS. All ions of a particular mass-to-charge ratio oscillate at a very specific frequency given a set of experimental conditions. These ions can be further manipulated by applying a frequency in resonance with their oscillation frequency. This is typically done at an amplitude great enough to cause unwanted ions to be ejected or an amplitude just high enough to cause fragmentation of the ions. By ejecting ions that are either unwanted or may be interfering with the ions of interest, or by generating specific fragment ions, an analyte's identity can be confirmed with higher specificity. By incorporating CIT technology into Griffin spectrophotometers, the vacuum requirements are also reduced and the power requirements minimized, thus achieving analytical performance and resolution equivalent to floor-sized quadrupole mass spectrometers.

General connection terms including, but not limited to "connected," "attached," "conjoined," "secured," and "affixed" are not meant to be limiting, such that structures so "associated" may have more than one way of being associated. "Fluidly connected" indicates a connection for conveying a fluid therethrough. "Digitally connected" indicates a connection in which digital data may be conveyed therethrough. "Electrically connected" indicates a connection in which units of electrical charge are conveyed therethrough.

Relative terms should be construed as such. For example, the term "front" is meant to be relative to the term "back," the term "upper" is meant to be relative to the term "lower," the term "vertical" is meant to be relative to the term "horizontal," the term "top" is meant to be relative to the term "bottom," and the term "inside" is meant to be relative to the term "outside," and so forth. Unless specifically stated otherwise, the terms "first," "second," "third," and "fourth" are meant solely for purposes of designation and not for order or for limitation. Reference to "one embodiment," "an embodiment," or an "aspect," means that a particular feature, structure, step, combination or characteristic described in connection with the embodiment or aspect is included in at least one realization of the present invention. Thus, the appearances of the phrases "in one embodiment" or "in an embodiment" in various places throughout this specification are not necessarily all referring to the same embodiment and may apply to multiple embodiments. Furthermore, particular features, structures, or characteristics of the invention may be combined in any suitable manner in one or more embodiments.

"Adapted to" includes and encompasses the meanings of "capable of" and additionally, "designed to", as applies to those uses intended by the patent. In contrast, a claim drafted with the limitation "capable of" also encompasses unintended uses and misuses of a functional element beyond those uses indicated in the disclosure. Aspex Eyewear v Marchon Eyewear 672 F3d 1335, 1349 (Fed Circ 2012). "Configured to", as used here, is taken to indicate is able to, is designed to, and is intended to function in support of the inventive structures, and is thus more stringent than "enabled to".

It should be noted that the terms "may," "can," and "might" are used to indicate alternatives and optional features and only should be construed as a limitation if specifically included in the claims. The various components, features, steps, or embodiments thereof are all "preferred" whether or not specifically so indicated. Claims not including a specific limitation should not be construed to include that limitation. For example, the term "a" or "an" as used in the claims does not exclude a plurality.

"Conventional" refers to a term or method designating that which is known and commonly understood in the technology to which this invention relates.

Unless the context requires otherwise, throughout the specification and claims that follow, the term "comprise" and variations thereof, such as, "comprises" and "comprising" are to be construed in an open, inclusive sense—as in "including, but not limited to."

The appended claims are not to be interpreted as including means-plus-function limitations, unless a given claim explicitly evokes the means-plus-function clause of 35 USC § 112 para (f) by using the phrase "means for" followed by a verb in gerund form.

A "method" as disclosed herein refers to one or more steps or actions for achieving the described end. Unless a specific order of steps or actions is required for proper operation of the embodiment, the order and/or use of specific steps and/or actions may be modified without departing from the scope of the present invention.

DETAILED DESCRIPTION

The foregoing and other objectives, features, and advantages of the invention will be more readily understood upon consideration of the following detailed description of the invention, taken in conjunction with the accompanying drawings, in which preferred embodiments of the invention are illustrated by way of example. It is to be expressly understood, however, that the drawings are for illustration and description only and are not intended as a definition of the limits of the invention.

FIG. 1A is a view of a conventional axisymmetric jet for particle sampling from surfaces. The figure is adapted from a published work [Keedy et al., Removal Rates of Explosive Particles From a Surface by Impingement of a Gas Jet. Aerosol Sci Tech. DOI 10.1080/02786826.2011.616920.] Gas is ejected under pressure from a generally round nozzle. The apparatus includes an air inlet, a reservoir 1102 for storing pressurized gas, a pressure regulator 1101, a pressure transducer 1103 and solenoid valve 1104 that controls release of air into the jet nozzle 1105.

Figure 1B:
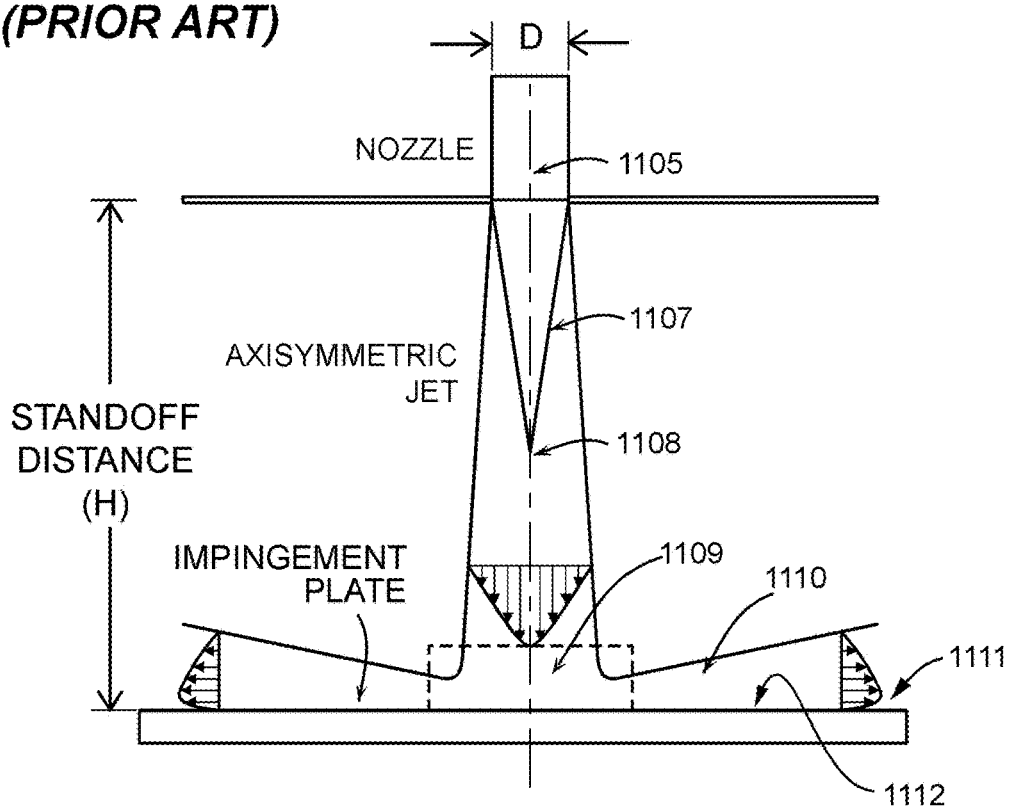

FIG. 1B is a cross-section through a representative conventional axisymmetric jet nozzle, with jet shape and structure illustrated schematically. The inside structure of the jet has been analyzed and includes a "core flow" region 1107 that expands into a "free jet" 1108 after exiting the jet nozzle 1105. On impact with a solid surface 1112, the jet is re-radiated all around the axis of flow. At the impingement point, a stagnation zone 1109 is observed and a lateral flow, termed here a "wall jet zone" (1110), develops on the surface. Velocities and shear are lower in the boundary layer 1111, as illustrated in FIG. 2.

Figure 2:
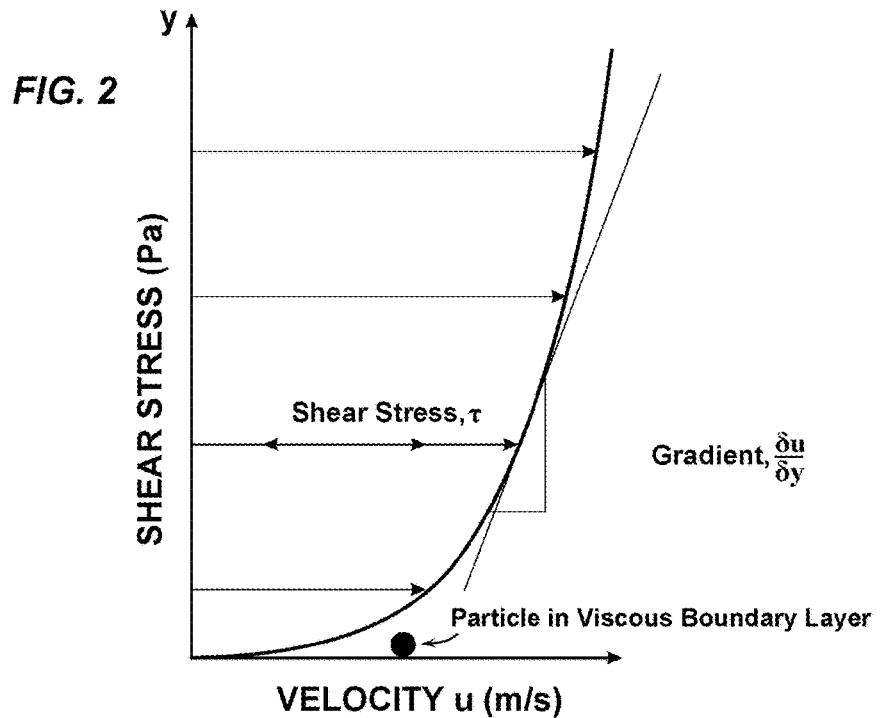

FIG. 2 summarizes key parameters that characterize the tool (i.e., gas flow) as used to improve particle mobilization and capture from a surface. Particle mobilization is in part a function of wall jet velocity and shear stress in the viscous boundary layer. Velocities are not plug flow, but may be characterized as bullet flow with drag when contacting the boundary layer. The effect of the flow on a particle is dependent on the particle's aerodynamic height and the depth of the boundary layer.

Figure 3A:
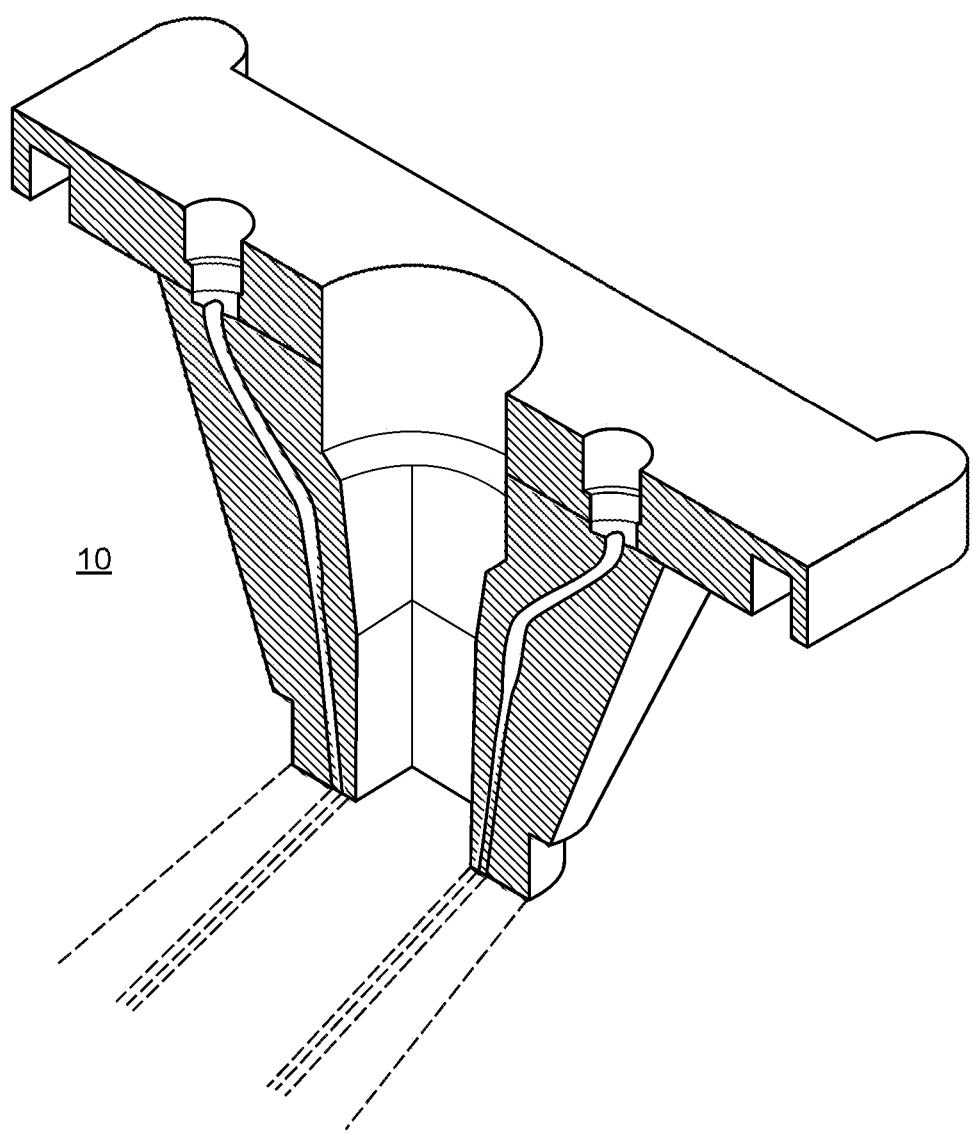

FIG. 3A is a CAD drawing of a first non-contacting sampler 10. Exposed on the open face is a cutaway view of a pair of slit jet apertures, one on each side of a central suction intake extending on a center axis from top to bottom. The phantom lines indicate that the slit geometry may be extended laterally to increase the aspect ratio of each slit jet orifice.

Figure 3B:
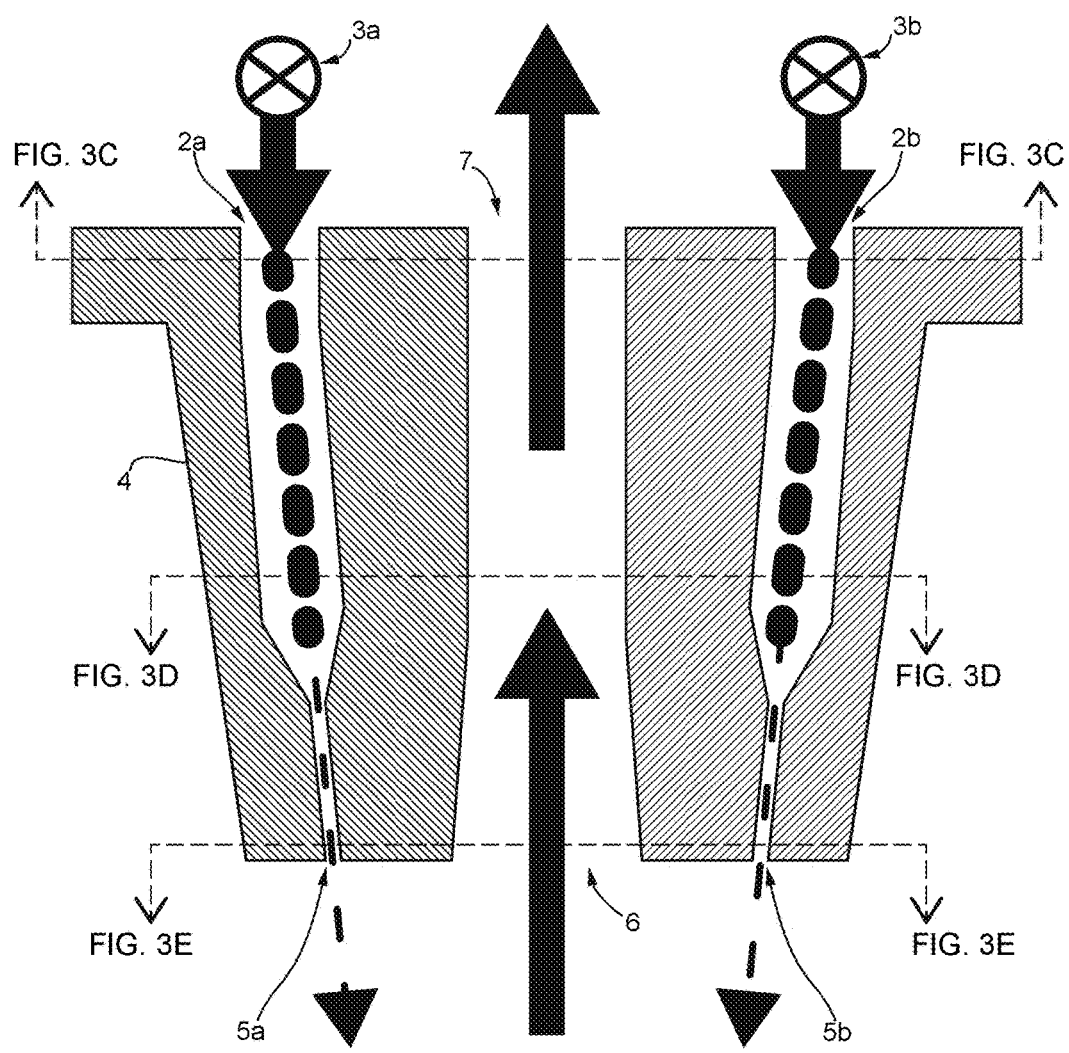

Aspirated gas moves from the suction port through the chimney or manifold and is exhausted through a suction pump such as a centrifugal blower or diaphragm pump (not shown). The two lateral ducts are slit jet apertures and extend from the upper surface of the sampling head to a slit on the lower surface. Gas is forced under pressure into the jet intake and is expelled as a planar jet burst or burst at higher velocity from the distal slit orifices. Pressure is equalized along the slit. FIG. 3B is a schematic showing the structure and operation of a representative non-contacting sampler nose with valves for delivering pulsatile planar jet bursts from slit jets 5a,5b. FIG. 3B shows a stack of cross-sections through a representative sampling head 10, with jet feed, valving, and suction port. Gas is forced through ducts 2a,2b under control of high speed valves 3a,3b. The ducts are formed in a non-contacting sampler housing body 4. Gas flow may be generally pulsatile (21, FIG. 4), and jet bursts exit the body at slit orifices 5a,5b. Gas and any suspended target analyte is collected at suction port intake 6 and is delivered to a downstream analytical module (not shown) through suction manifold 7. Three sectional views are marked in FIG. 3B and are discussed below.

Figure 3C:
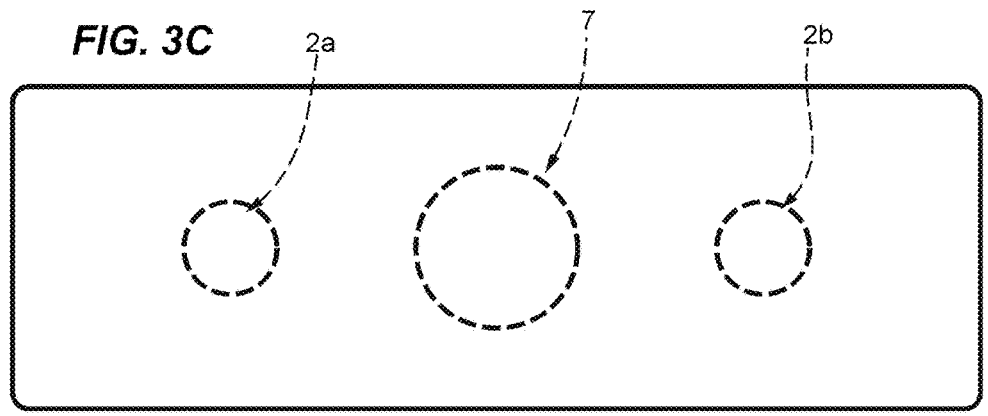
Figure 3D:
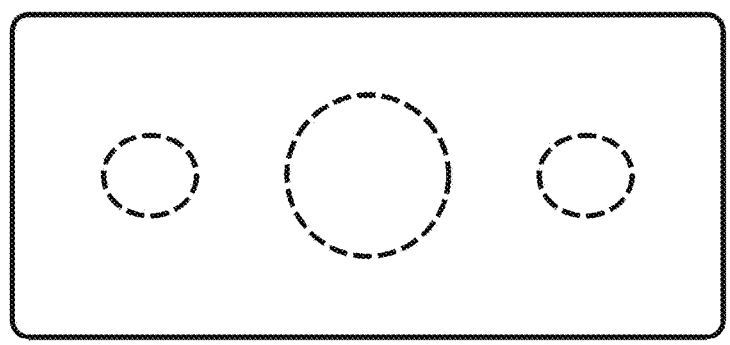
Figure 3E:
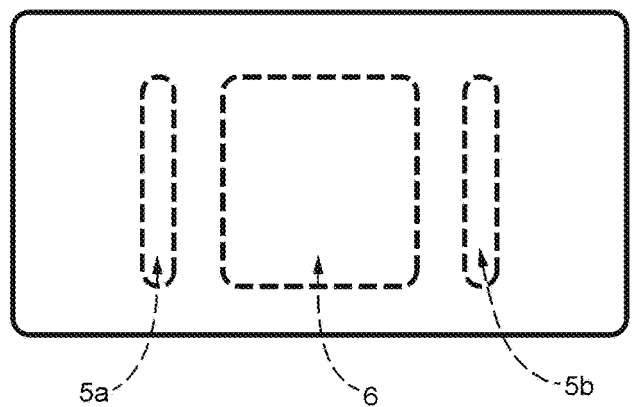

FIGS. 3C, 3D and 3E are representative sections through a non-contacting sampler head assembly with jet outlets and suction intake. Sections are taken from top to bottom as shown in FIG. 3B. Next, FIGS. 3C, 3D and 3E are views at three planes along the primary long axis of the non-contacting sampler head. The jet intake ducts 2a,2b are marked as before on the top face of the head in FIG. 3B. The central suction manifold 7 is also shown in plan view. FIG. 3D is a view midway through the length of the nozzle and shows each of the ducts to be generally circular in shape. At the jet orifice exit, as shown in FIG. 3E, the jet ports (5a,5b) are distinctly slit-like and are designed to emit a jet burst having the characteristic shape of an air knife in this instance. To streamline the gas suction return, the suction port on the lower face of the nozzle is rectangular or square in plan view but may be tapered or conical.

Figure 4:
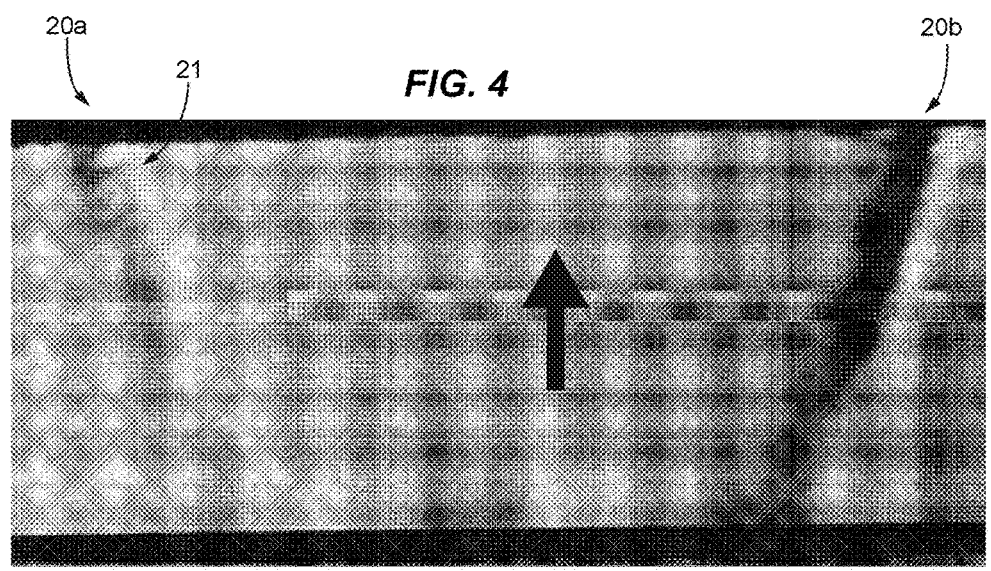

FIG. 4 is a Schlieren image of two convergent planar jets (21a,21b) emitted from representative slit jet apertures of the invention and impinging on a solid surface. Visible between the impinging jet cores are lateral wall jets colliding and lifting up (bold arrow) as a turbulent air mass directed into a suction intake in the center between the jet cores.

Figure 5A:
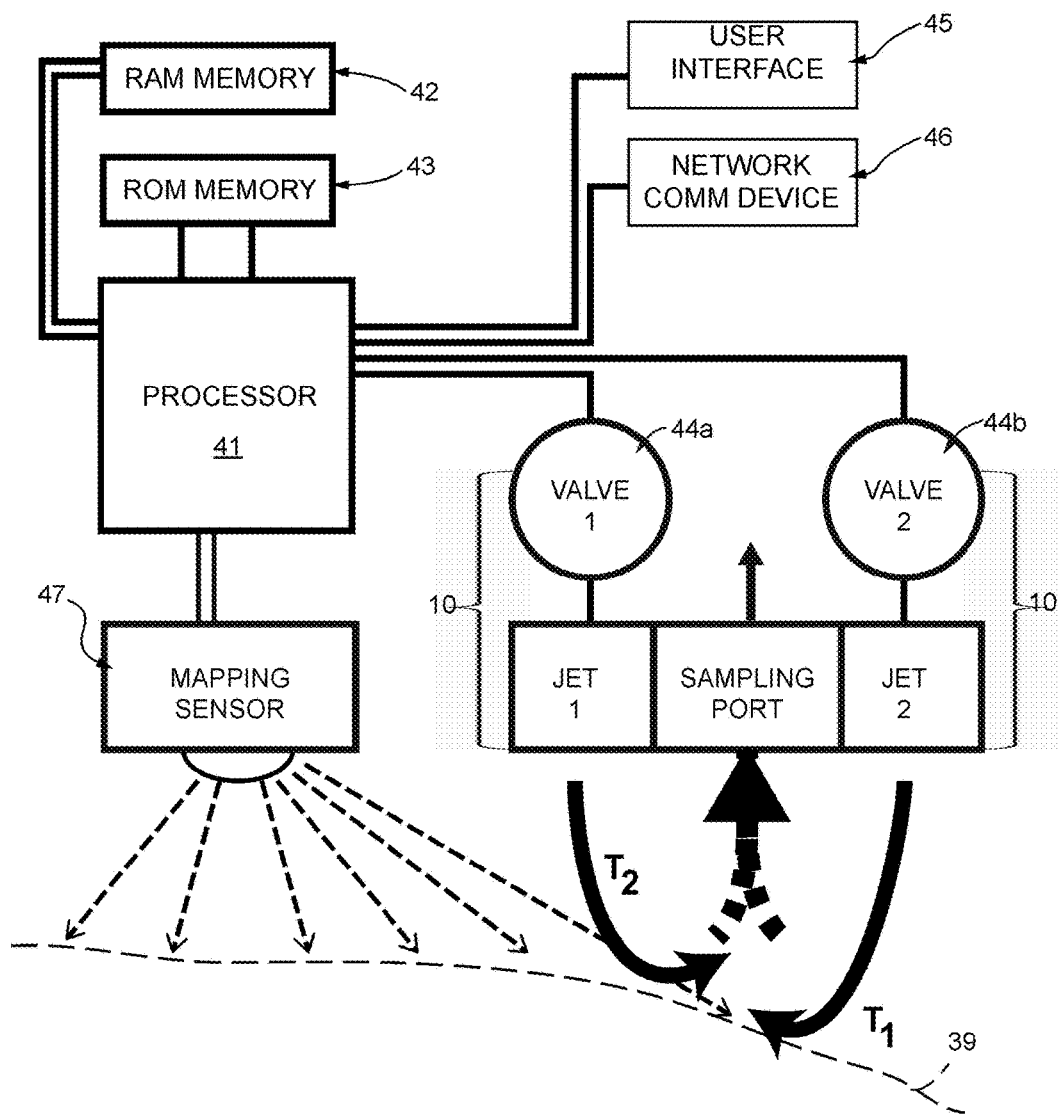

FIG. 5A is a block diagram of a "smart jet" apparatus 40 configured to use sensor data to map a substrate surface and coordinate activation of opposing jet nozzles so as to optimize sample entrainment in a suction port. In addition to the non-contacting sampler head assembly (10, brackets), a mapping sensor module 47 is also shown. The mapping sensor is essentially a range finder that operates to map any contours in the surface being sampled (39, dashed line). Typically, this may be done with a scanning laser system, for example. Data from the sensor module 47 is fed to a processor 41 which operates with memory elements 42,43 and is provided with an instruction set to calculate jet burst timing from the contour of the target surface and to convey targeting and timing commands to each of two high speed valves (44a,44b) that control the jet bursts. The suction port operates as described above. In this representative apparatus, a user interface 45 and network communications port 46 are also provided.

In operation, high-speed valves are triggered to create waveforms of high velocity pressurized jet bursts. Individual jet bursts may be synchronous, asynchronous and coordinated so as to direct samples to a suction port from an irregular surface. Computerized systems for controlling the jet bursts may include sensor mapping for determining the proximity, angulation and fine structure of the substrate surface in three-dimensions.

The apparatus can be fully automated or can be operated with a trigger such as in a sampling gun. Fully automated versions may be suspended for example from a boom, and may be advanced in front of a vehicle or steered robotically when inspecting enclosed spaces. While not shown, a camera or other sensor may also be included and smart imaging technology deployed to recognize suspicious forms such as evidence of recent digging or packages that seem out of place.

The jet bursts may be synchronous, but more advantageously may be timed in series to optimize uplift of sample particulates and vapors dislodged from the target surface 39. If for example a tilted surface is encountered, firing a first pulse jet burst above the target center at an angle causes a diversion of the jet downhill and toward the target center. A second, stronger pulse jet burst is then sent a few microseconds later, and intersects and goes under the first jet burst, causing the initial more concentrated sample material to rise up and roll like a horizontal cyclone, while entering the zone where it is sucked into the intake 6 of the suction port. The concentrate is then carried to an analytical module or sampling station for further processing.

The jet burst timing would be re-calculated and reversed if the tilt of the substrate surface 39 were reversed, and dropped to the left instead of the right. Thus the timing of jet $T_1$ and jet $T_2$ is under the control of processor 41, which performs a complex calculation based on the underlying geometry in order to optimize the smart jet sequence. When more than two jets are utilized, yet more complex calculations are driven by the sensor data and map of the contours of the surface.

Significant parameters in optimizing a sampling system using smart jets include jet reservoir gauge pressure and the slit "diameter" $L_c$, jet nozzle inlet pressure and pressure drop, jet angulation and standoff distance, jet aspect ratio, and jet geometry. Representative wall shear stress and wall jet velocity profiles will be shown below.

Figure 5B:
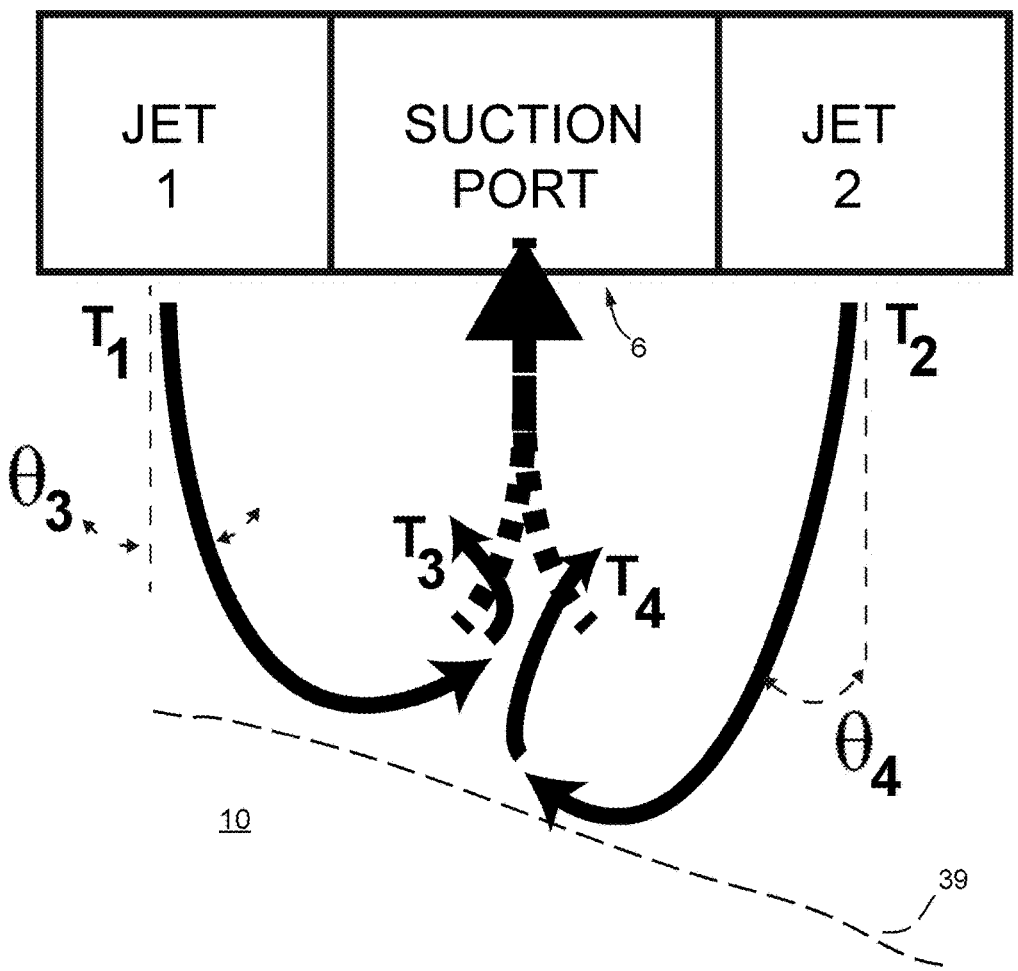

FIG. 5B is a schematic view in close-up, showing asynchronous jet burst activation and control of angulation on a sloped surface 39. The basic non-contacting sampler configuration 10 includes two slit jets (JET 1, JET 2) separated by a central sampling intake. The slit jets are angled to converge at a distance below the surface to be sampled and uplifted air is forced into the sampling intake.

Angles $\theta_3$ and $\theta_4$ are varied by adjusting the jet burst timing and amplitude. With more advanced robotics, jet angulation may be mechanically changed on the fly in response to a sensor map of the surface being sampled. Alternatively the entire non-contacting sampler head 10 can be tilted to follow a sloping surface. Jets $T_1$ and $T_2$ both strike the surface and are deflected, continuing as jets $T_3$ and $T_4$.

Figure 6:
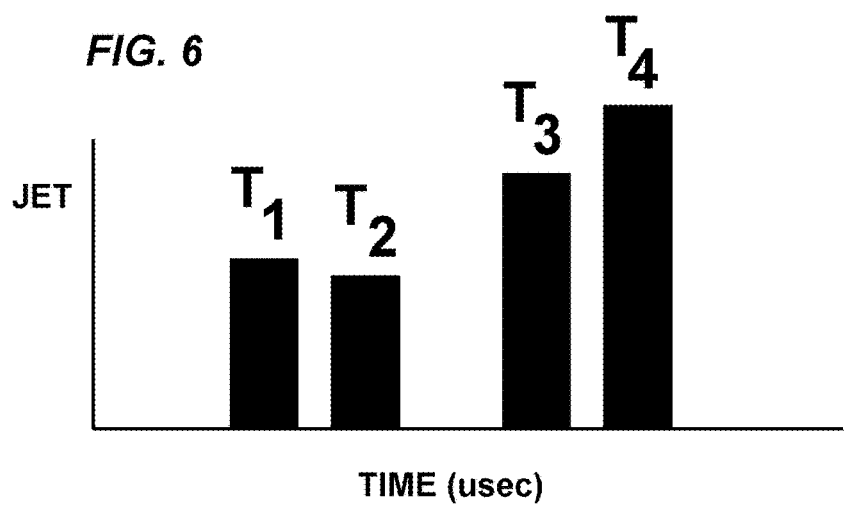

FIG. 6 is a plot showing the timing of jet bursts $T_1$, $T_2$, $T_3$ and $T_4$. Time spacing and duration may be synchronous or asynchronous, and is calculated to optimize valve actuation for collecting a sample. Timing, duration, angulation and amplitude may be controlled by computerized solenoids or using robotic arms. Feedback sensor loops may also be employed to ensure that jets $T_3$ and $T_4$ are captured in the intake port.

Figure 7:
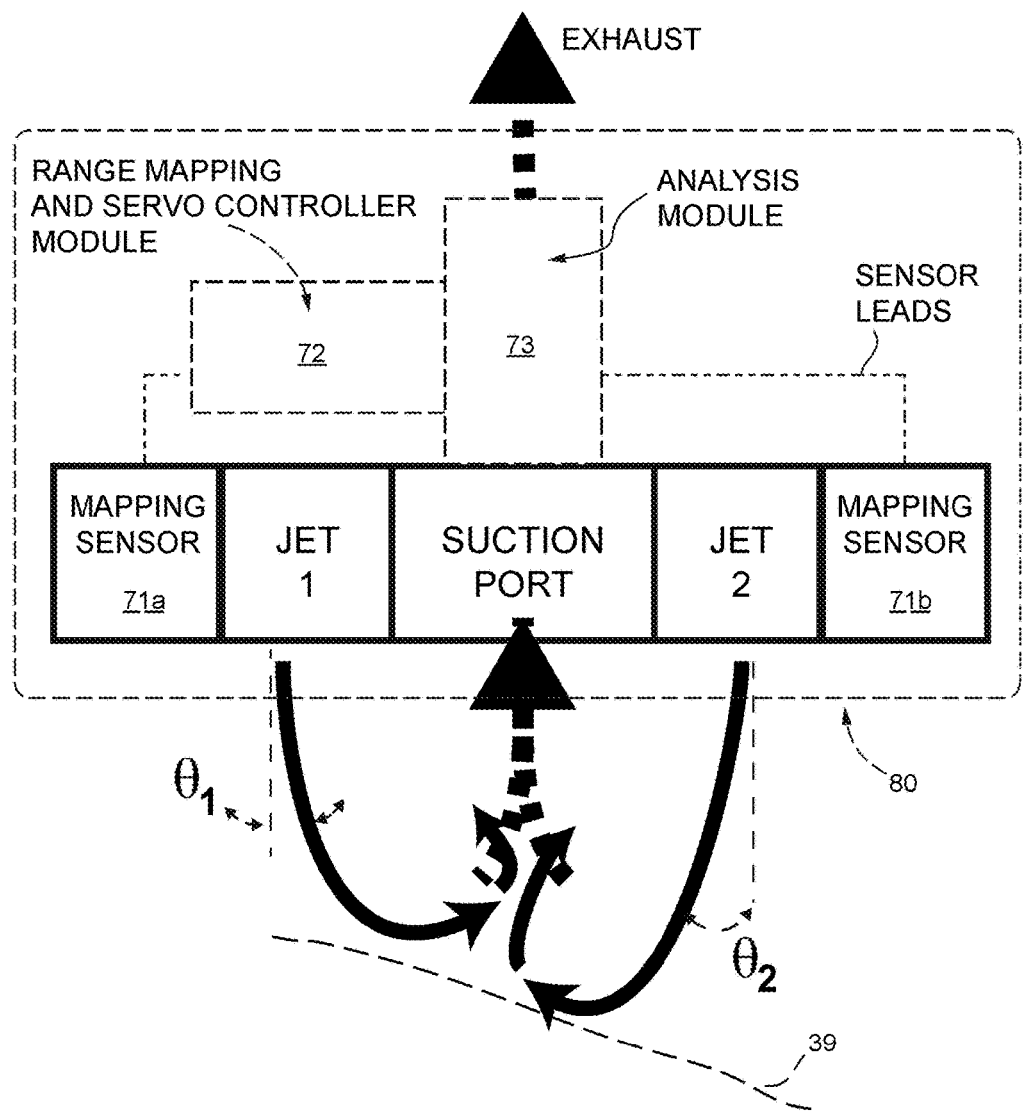

FIG. 7 is a schematic view of a more complex slit jet apparatus 80 with contralaterally disposed mapping sensors (71a,71b), a range mapping module 72, and analysis module 73 in a single package. Angles $\theta_1$ and $\theta_2$ are controlled by changing the angulation of the jet, the timing or amplitude of the jets, or by tilting the non-contacting sampler head on an arm. In this view, sensor data is supplied to the range mapping module 72 that controls servos responsible for jet burst timing (and optionally angulation). Sensor data is also supplied to the analysis module 73, where suspicious aspirates may be concentrated and isolated for further analysis, such as by methods known in the art.

More than two jets may be controlled using this system, but for simplicity of explanation, the illustration is limited to two jets, JET 1 and JET 2. Also shown are a pair of mapping sensors (71a,71b), one on either side of the sampling head. Mapping data is fed from the right and left sensor clusters into a range mapping and servo controller module, which plots a three-dimensional contour of the surface to be sampled and enters a set of jet timing parameters into the servo controller. The servo controller executes the sampling strategy by opening high speed valves to release jet bursts at controlled times. Jet action is as described before. Exhausted air drawn through the suction intake has transited an analysis module and downstream processing, concentrating, and analysis is completed by methods known in the art.

Figure 8:
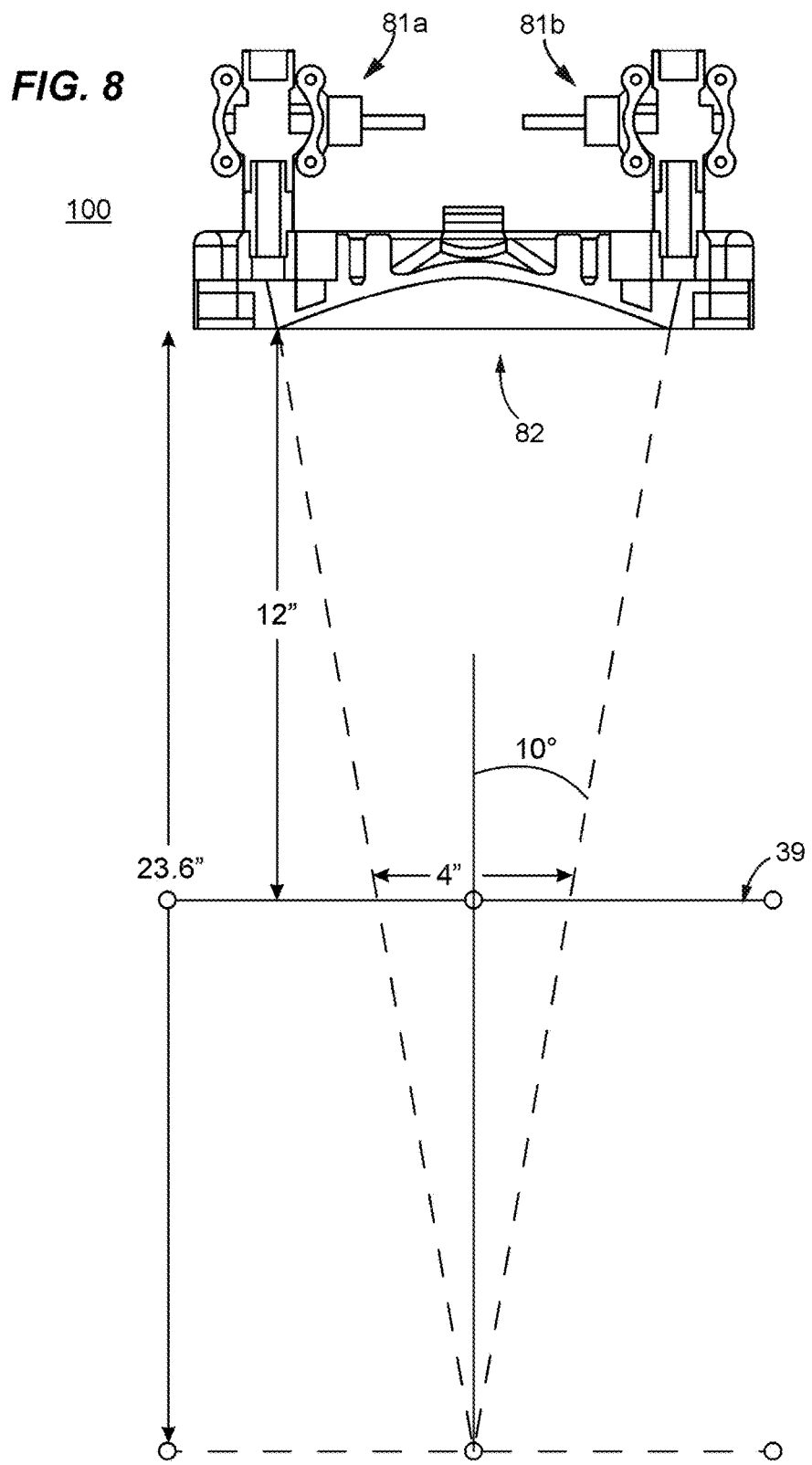

FIG. 8 is a representation of a sampling head 100 with high speed valves (81a,81b) and dual jets having an opposing angulation of 10° from plumb, and shows a standoff distance to sample of twelve inches versus a convergence distance of about twenty-four inches. A "reach" of four inches in breadth of sampling area is achieved in this example. These measurements are derived from an early prototype and the invention is not limited to these dimensions or configuration.

By angling the slit jets 101, a "standoff distance" is established such that the two jets intersect at a defined distance from the lower end of the sampling head. The intersection point is a virtual point below the substrate surface 39. Generally the intersection distance for a slit jet array is at least or greater than nine inches, more preferably greater than twelve inches and preferredly equal to or greater than eighteen inches. The "reach" defines the distance between the jets at impact, and is typically much larger than obtained with other jet types. While a reach of four inches is shown here, much larger areas or much smaller areas may be sampled.

Figure 9A:
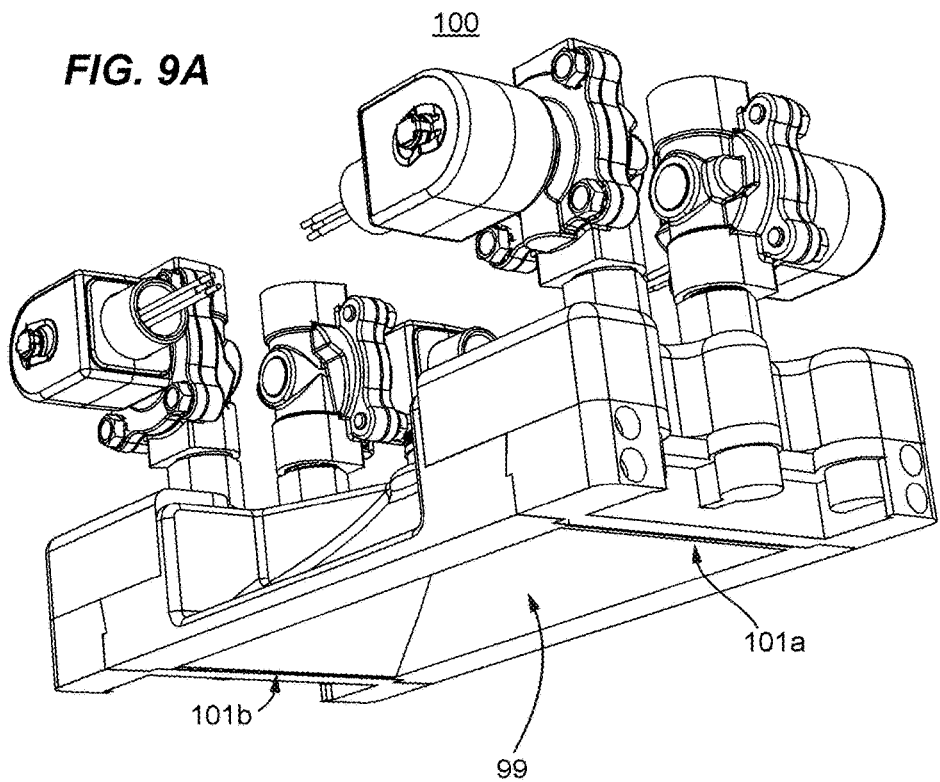
Figure 9B:
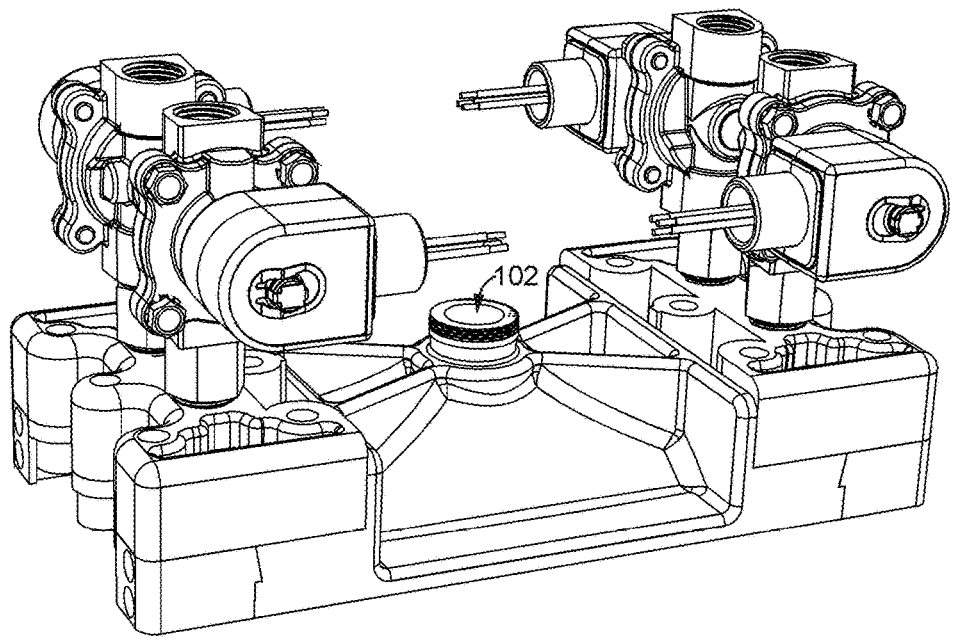

FIGS. 9A and 9B are perspective views a non-contacting sampler head 100 with a quadruplex jet array having two pairs of slit jets (101a, 101b) around a central suction intake. In the first view, the large suction intake bell 99 of the non-contacting sampler head assembly is visible as sloping planes. In the second view, the common center port 102 of the suction inlet is visible (without connection) and four high speed valves are mounted, one above each of the jet apertures. The four slit jets are arrayed on either side of the intake port. Bundles of wires 104 to a controller are also represented without connections (but are connected to a computer or controller for controlling the valves and the head pressure in the jet manifold).

FIGS. 10A and 10C are isometric views of the underside and the top of the quadruplex jet array and non-contacting sampler head assembly 100 of the preceding figure. The aspect ratio of each jet 101 is very high at the aperture as demonstrated in detail view FIG. 10B (circled and magnified). Each jet extends along the contralateral edges of the central suction intake 102.

Figure 11A:
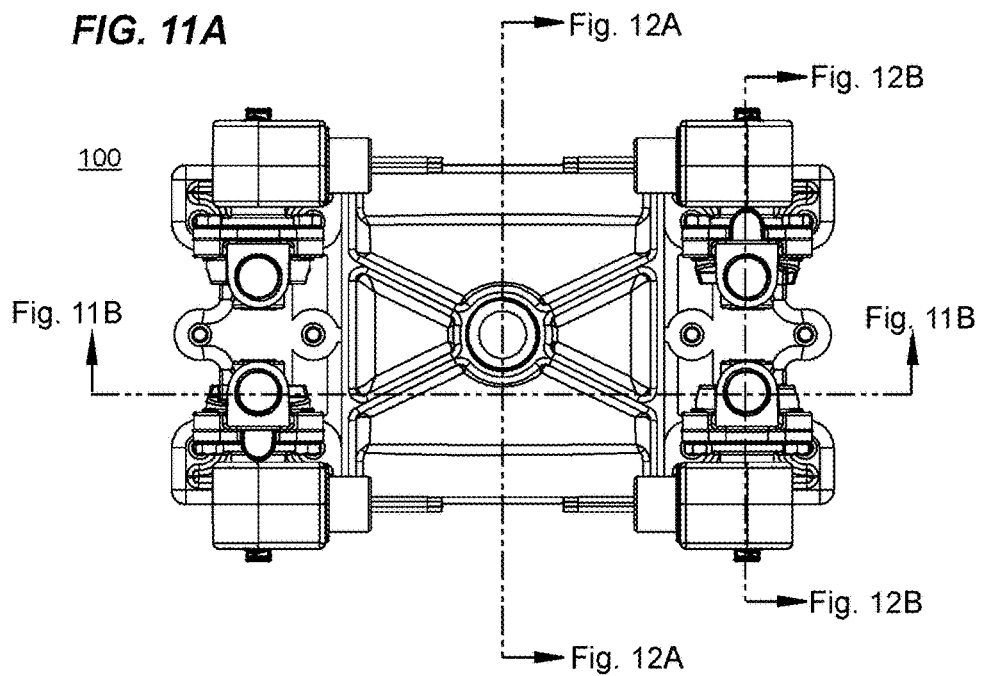
Figure 11B:
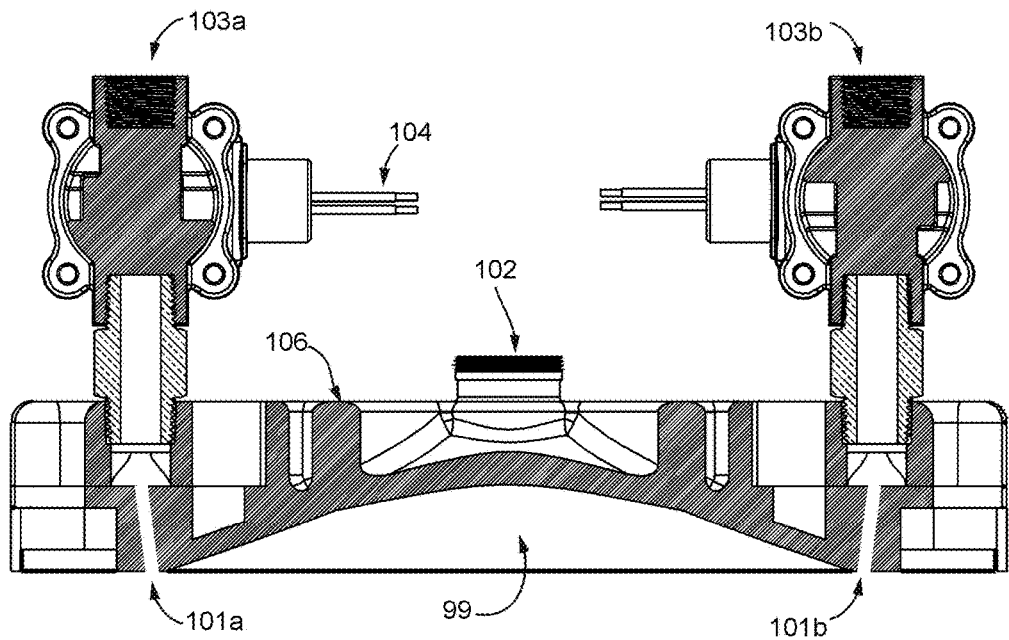

FIG. 11A sets up a series of section planes, beginning with the long axis offset sectional view of FIG. 11B. Here the jet aperture size (101a, 101b) is exaggerated for clarity, but the convergent angulation and proximity to the center suction intake are represented as a working model. Also shown are valve trees (103a,103b). suction intake bell 99, suction intake port 102, wire harnesses 104, and non-contacting sampler housing body 106.

Figure 12A:
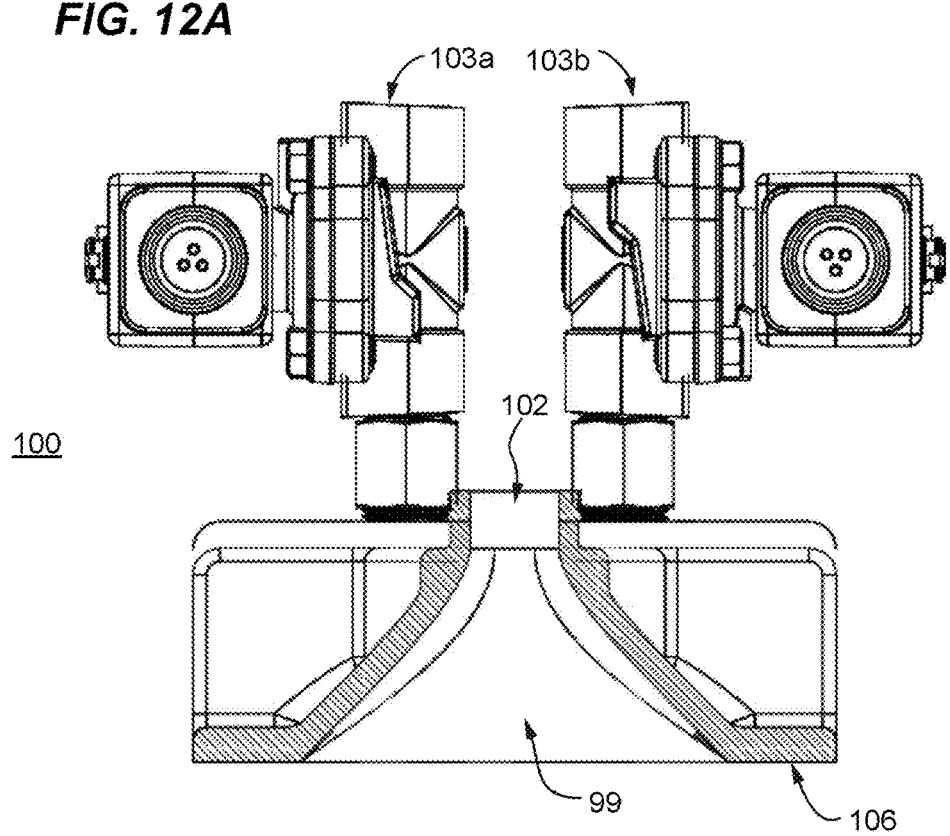
Figure 12B:
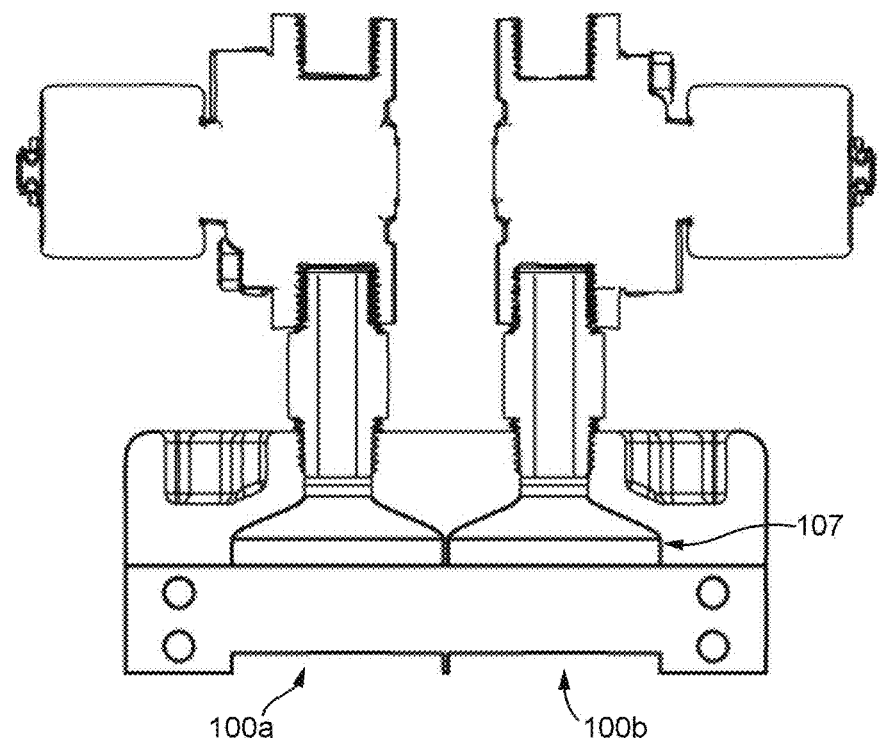

FIGS. 12A and 12B are sections taken through the non-contacting sampler head assembly. In the first view, the cut plane is perpendicular to the long axis section depicted in FIG. 11B and intersects the suction intake port 102 and suction intake bell 99. In FIG. 12B, the cut plane goes through the valve trees (internal detail not shown). Threaded fittings are represented but those skilled in the art are able to devise other tubular unions. The section continues through the jet feed ductwork to the jet manifolds (107, for pressure equalization), and cuts through the pair of jet apertures (101a,101b) at the base of the structure so as to illustrate the aspect ratio of the jet length versus width; referencing also FIG. 10B.

Figure 13A:
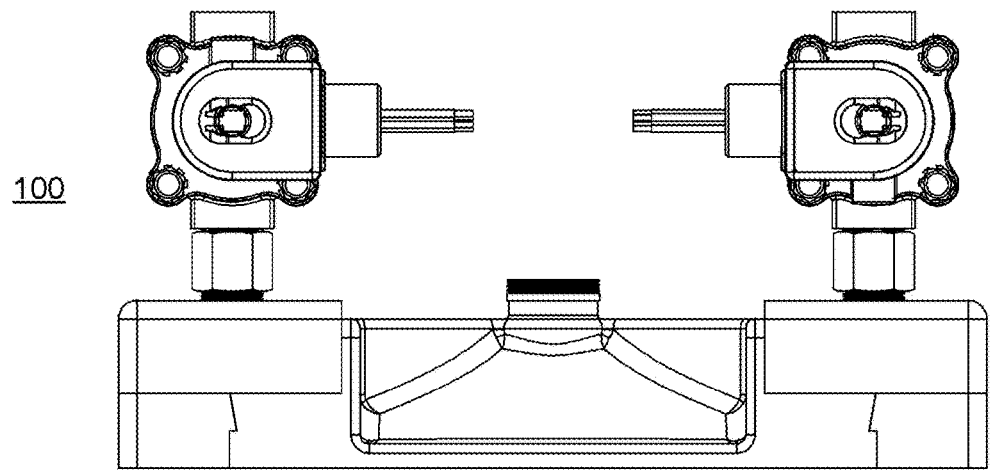
Figure 13B:
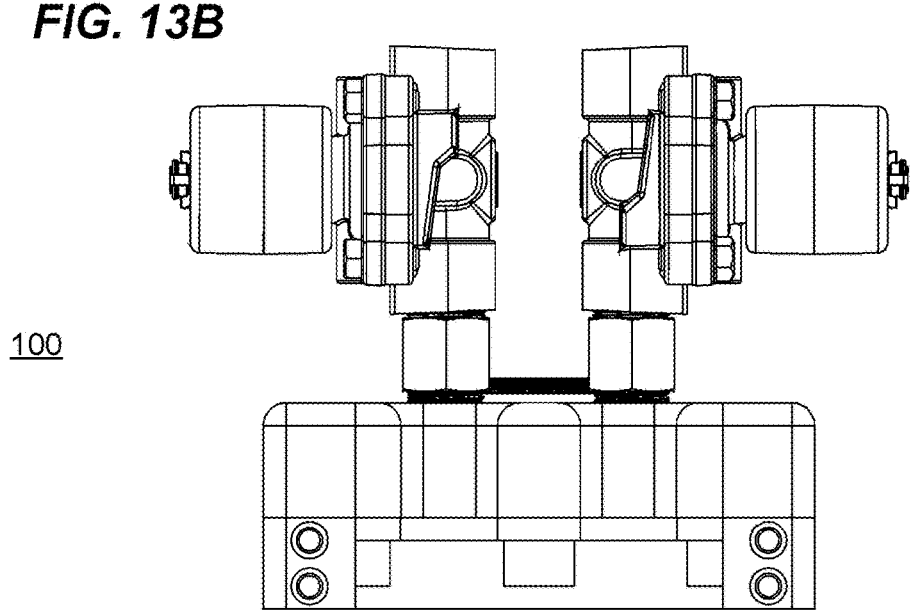

FIGS. 13A and 13B are side and end views of the non-contacting sampler head assembly 100. These views are of the working prototype represented in FIGS. 9A through 13B.

Figure 14:
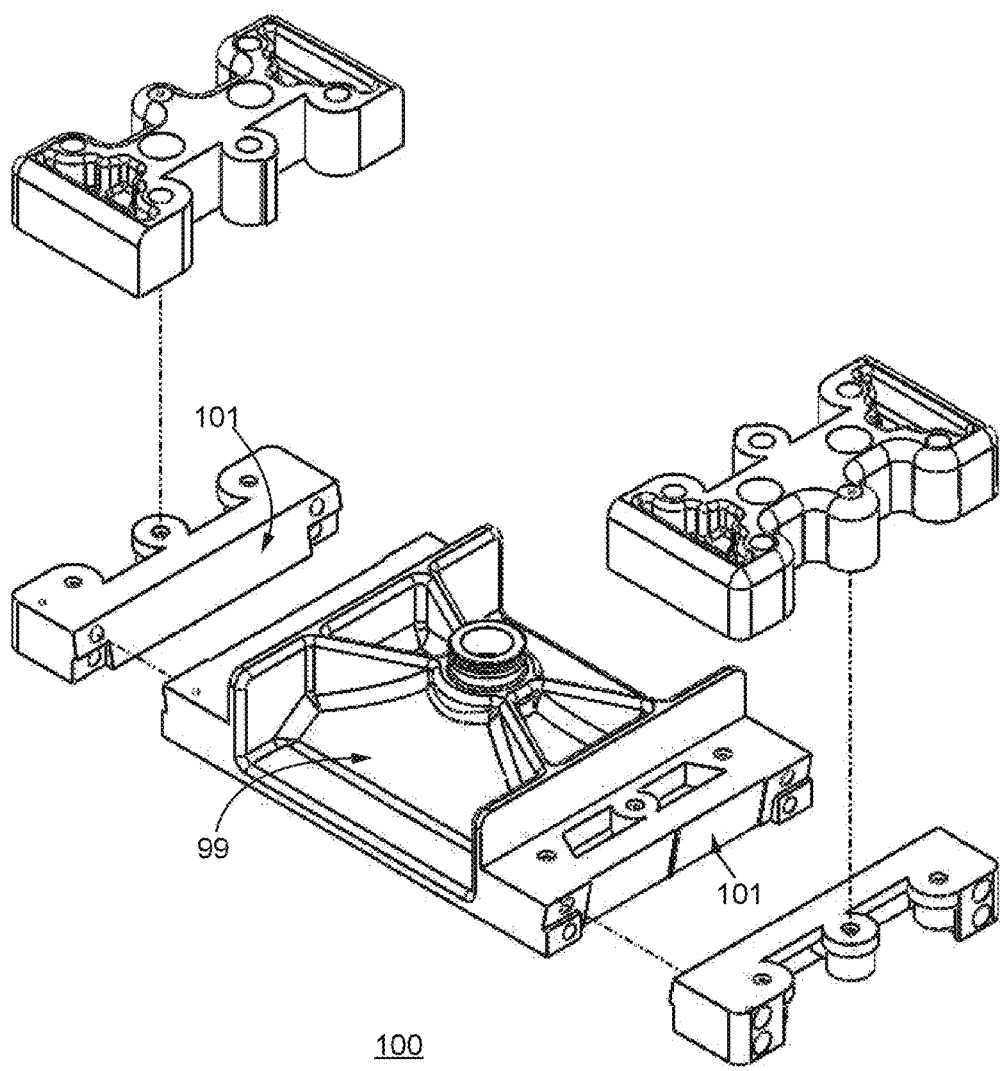

FIG. 14 is an exploded view showing assembly of a non-contacting sampler head with high aspect ratio jet apertures 101. The valve trees are not shown for clarity. The sampling bell 99 is shown in relief on the backside of the non-contacting sampler housing body.

Figure 15A:
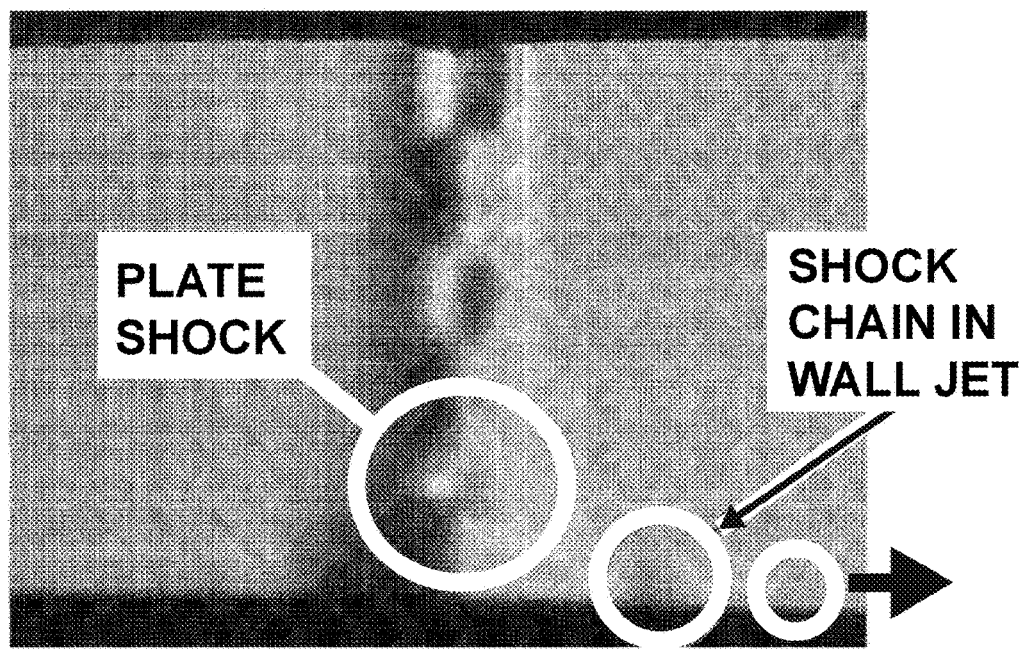
Figure 15B:
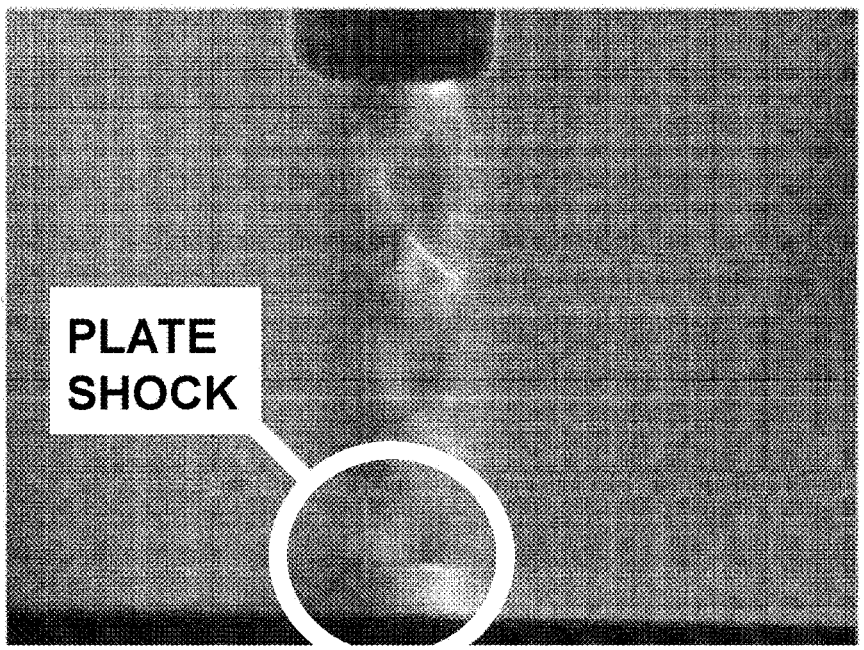
Figure 16A:
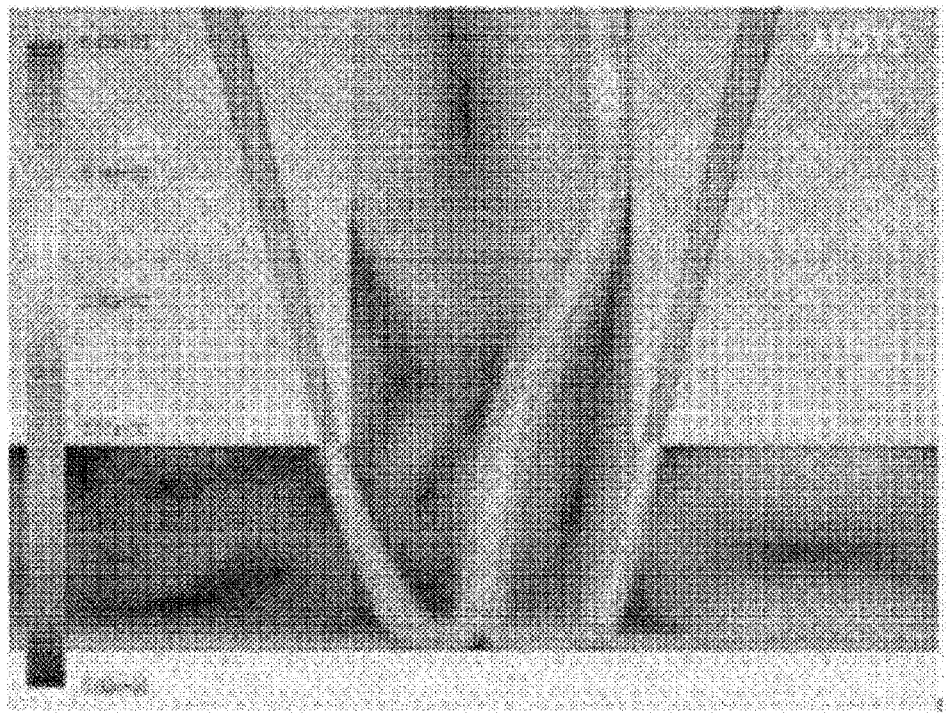
Figure 16B:
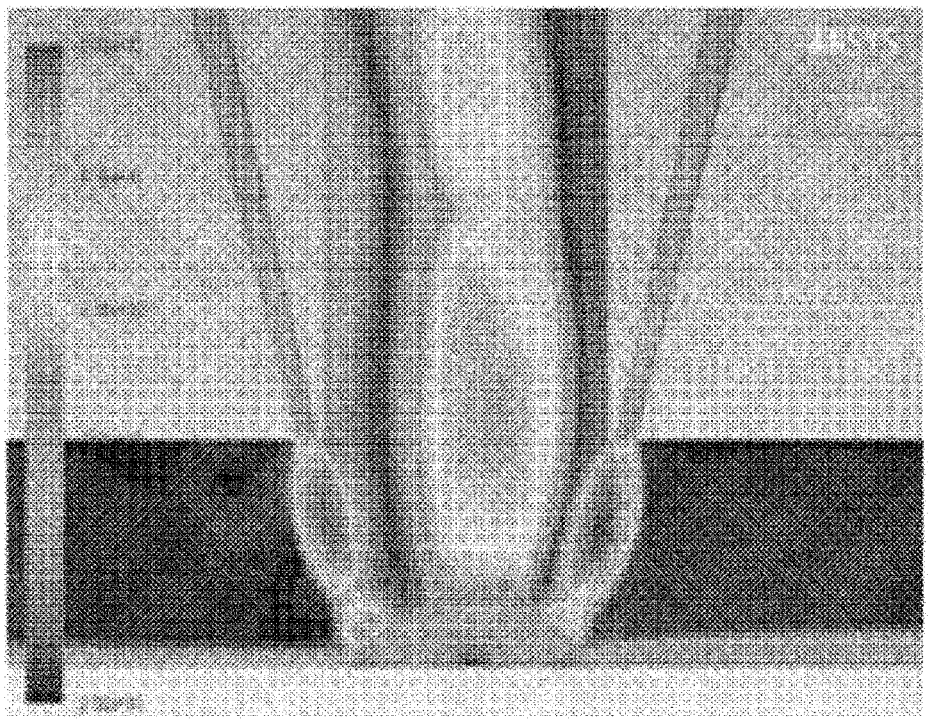
Figure 17A:
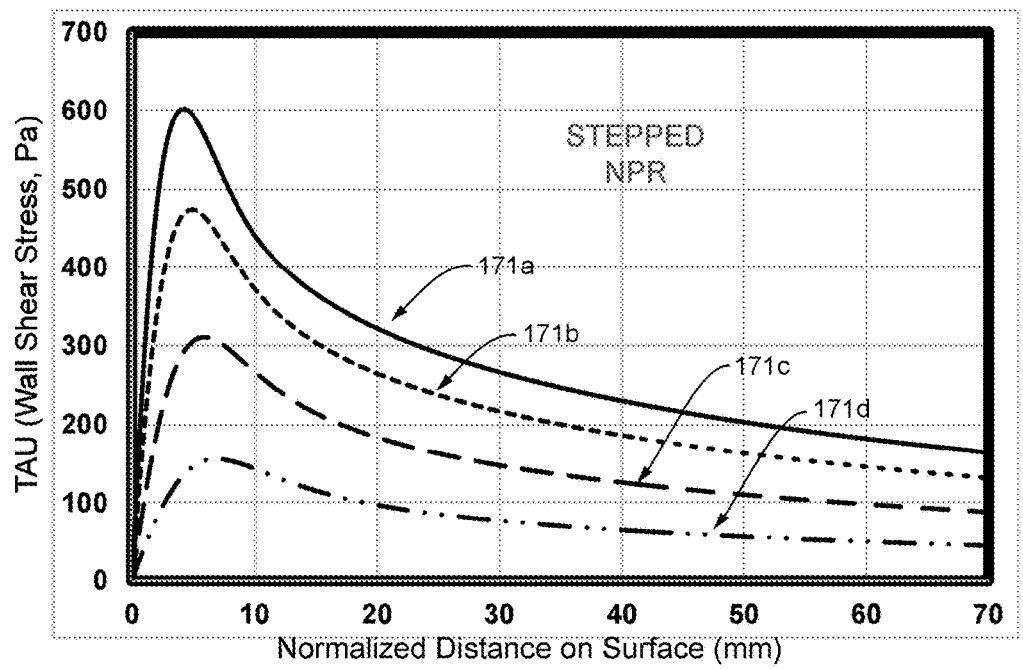
Figure 17B:
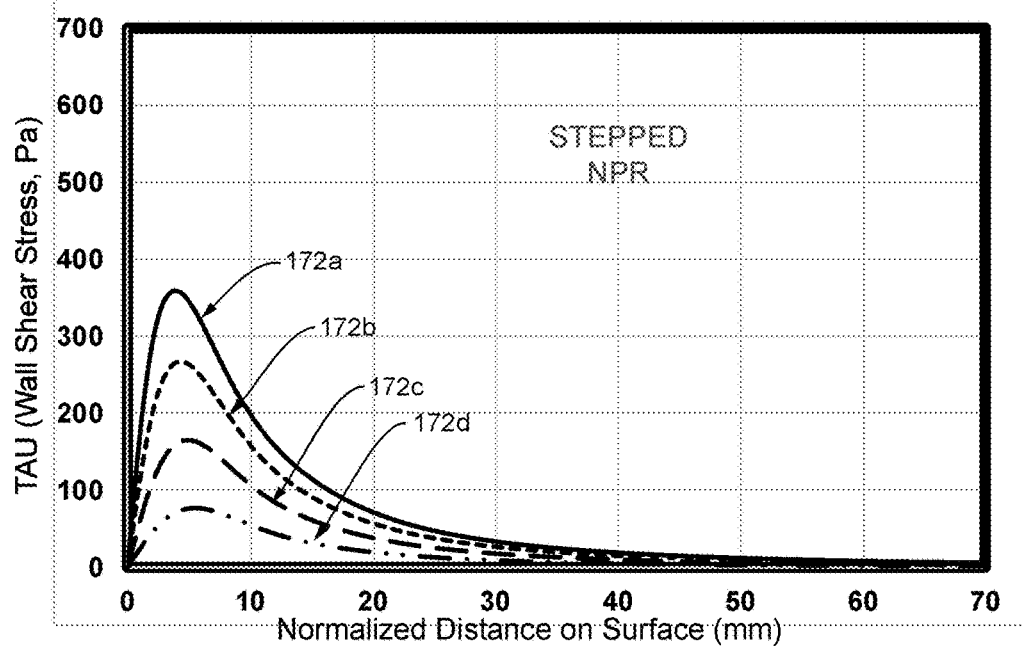

FIGS. 15A and 15B are Schlieren images of impinging jets in which free jet, and wall jet regions are visible. A comparison is shown between a slit jet of the inventive sampler head (FIG. 15A) and a conventional nozzle jet of equivalent aerodynamic diameter (FIG. 15B). Plate shock occurs with both jets, but the slit jet in addition shows the presence of shock and expansion waves in the wall jet that are not detected for the axisymmetric jet. This indicates higher velocities and higher wall stresses on the interrogated surface. Slit jet shock trains result in localized recirculation within bubble-like shock fronts at the impacted surface. This novel behavior is amplified in the wall jet when the jet orifice is angled from vertical. Each shock front is a result of a flow transition to supersonic velocity, resulting in conditions beneficial for resuspension of particles as small as one micron in aerodynamic height. The viscous sub-boundary layer is 10-50 microns deep, but is stripped away by the shock-thereby providing large aerodynamic forces required for particle resuspension and delivering particulate and vapor analytes from surface into the suction intake.

At greater distances from impingement location, the wall jet flow in FIG. 15A is essentially in linear decay with extended reach and duration along a front extending to the right and left as depicted here. In contrast, the axial flow jet has a prominent plate jet shock, but is dissipated and decays exponentially to lower velocities very quickly in all directions.

Axisymmetric jets are characterized by a stagnation zone at the point of impact, but by angling slit jet bursts, a stagnation zone is weaker than in planar jets setup, storing less internal energy that can be converted to kinetic energy of the wall jet. Where two opposing wall jets meet, a stagnation zone forms at the collision point, but is turbulent and the rising uplift in the jet flow carries particles and vapors up into the intake.

While not bound by theory, the slit jet imposes linear flow in the wall jet region, and therefore the jet cannot expand in all directions (as from an impinging round jet). By conservation of momentum, a supersonic slit jet orifice produces a wall jet that contains all the momentum of the free jet and core, and thus will achieve shock fronts in the boundary layer, leading to increase in local wall shear stress. These flow structures are observed in the Schlieren images as a chain of shock fronts visible as rapid changes in density. The "shock train" causes boundary layer separation from the target surface and increases shear stress locally, yielding much higher particle removal What is surprising is that at all pressures considered (10-100 psig), wall shear stress (Pa) decays by jet expansion in an almost linear profile for an extended range. The shock in the boundary layer, this boundary layer separation is observed at the moderate slit jet orifice pressures of 40-60 psig, or even 20-30 psig.

In contrast (FIG. 15B), wall jet shear falls quadratically and the increase in inlet pressure (even above 100 psig out of a round nozzle) cannot extend the range of the wall jet. At the higher nozzle pressure, the combination of jet expansion and the jet energy is lost in shock structures in the free jet region which act as parasitic losses and are not effective in converting the jet momentum to the high velocity flow near the wall. Thus any additional pressure applied to the jet has little effect in developing a high velocity wall jet and does not add to the particle removal potential. Losses in the free jet expansion also limit the standoff height that can be achieved with round jets.

In contrast, the slit jets have a higher conversion efficiency of orifice velocity to wall jet velocity. Velocities above 100 m/s can be achieved in the compressible and underexpanded region of the wall jet flow. Decreasing H/D ratio (i.e., the ratio of standoff height H over hydraulic diameter D) is more effective in increasing wall jet velocity than increases in inlet pressure. The significance in terms of the power requirement needed to operate fully portable sampling device is clear. The prospect of battery operated, hand-held non-contacting samplers with low power consumption and extended battery life is now entirely feasible.

FIGS. 16A and 16B are computational fluid dynamics (CFD) simulations of opposing slit jets. The model uses essentially the same setup as depicted figuratively in FIG. 8. Two views are shown, one at lower pressure and one at higher pressure. A central suction inlet draws the jets into a particle and vapor collector. At lower pressure (about 20 psig), the suction return wanders as the stagnant layer and impingement points may shift. No plate shock is seen, but upward flow into the suction port is surprisingly organized and consistent with efficient particle recovery. At 80 psig (FIG. 16B) the free jet expansion region is seed shaped and terminates in a plate shock that serves as a sort of elbow to translate the flow into a horizontal wall jet. The free jet region is coherent and lacks the shock regions characteristic of axisymmetric jet nozzles. The stagnation region is relatively fixed when using two balanced opposing jets, but highly collimated flow continues up into the suction intake, suggesting very efficient removal and capture of particles on the surface.

For this work, the standoff distance is six inches. Slit jet critical dimension is limited from 3 mm to more preferably about 0.5 mm, and most preferably less than 1 mm, but the actual number chosen is dependent on the available gas flow rate and gas pressure. In general, higher standoff distances can be achieved for planar jet orifices by increasing jet velocity as jet L, increases by introducing a larger nozzle width or increasing pressure. These simulations are confirmed experimentally as shown in FIG. 18.

FIGS. 17A and 17B are CFD plots of wall shear stress (τ, Pa) at four different normalized pressure ratios (NPR). The top plot (FIG. 17A) shows the data (171*a*,171*b*,171*c*,171*d*) for a slit jet at a series of NPRs; the bottom plot (FIG. 17B) shows qualitatively and quantitatively contrasts the data for the two jet configurations. Surprisingly, with slit jets, wall pressure has an unexpected "reach", here extending well over 50 mm at substantial shear wall stress (~200 Pa). In comparison, the wall jet shear of the round jet (FIG. 17B) is essentially zero at 40 mm and is much lower even at 1 cm from the impingement point. Distance from impingement point is plotted (172*a*,172*b*,172*c*,172*d*), showing a dramatically improved profile with the slit jet pair. Surprisingly, this extended wall jet behavior is observed even at lower input pressures.

FIG. 18 is a montage of photographs taken with a high speed camera. Defined particle populations have been deposited on an impact plate for purposes of visualization of the lift-off. The experimental result is clearly copacetic with the computer simulation. Particles are seen to rise in a vertical draft into the suction intake port after efficient mobilization on the impact surface.

Although 20 um spherical silica particles were used to obtain the photographs, particles as small as one micron behave in the same way.

Taken together, these experimental and simulation results show (i) an increase of particle removal forces in the under-expanded region of axisymmetric and planar jets (slit jet apertures) where the underexpanded region is a function of nozzle pressure and the H/D; (ii) a longer underexpanded region in the planar jet configuration for the same pressures, (iii) significantly higher forces acting on the particle (shown in velocities and wall shear) in the wall jet region for the planar "slit jet" configuration. From these design considerations, the planar jet configuration has shear values above the threshold value for particle removal at longer stand-off distance/or lower operating pressures. Moreover, and importantly, the planar jet produces higher shear forces much farther away from its impinging point-extending the "reach" factor for the non-contacting sample collector.

FIGS. 19A and 19B are plots of wall shear stress ($\tau$, Pa) at higher normalized pressure ratios (NPR) to demonstrate that increased jet pressure does not remedy the deficit in reach of the wall jet for axisymmetric jets. Counterintuitively, increasing the jet pressure (192a, 192b) fails to generate a wall jet that is effective in removing particles outside a small 2 cm zone. This is true even though the peak wall shear is slightly higher for the axisymmetric jet very close to the impingement point (FIG. 19B). Outside that zone, jet force drops rapidly according to the r-squared law.

In contrast, as shown in FIG. 19A, the lateral wall jets generated in the slit jet configuration continue with $\tau$>100 Pa well past five centimeters (191a,191b). The level wall pressure is almost linear, and suggests a highly coherent wall jet with substantial force and velocity in intimate contact with the surface; stripping off the boundary layer. This is surprising because it can be achieved at lower pressures than have conventionally been applied with axisymmetric jets.

Figure 20A:
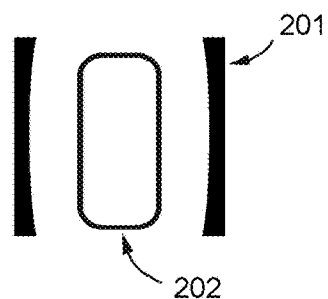
Figure 20B:
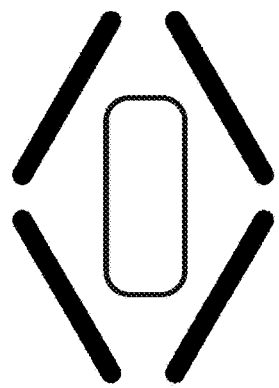
Figure 20C:
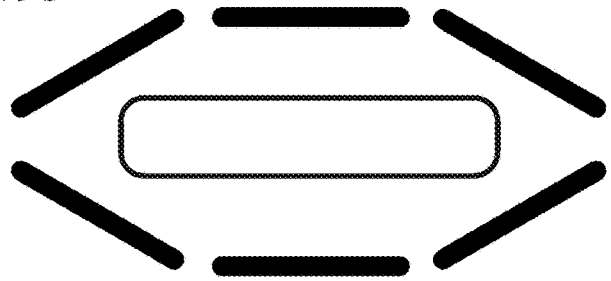
Figure 20D:

FIGS. 20A, 20B, 20C, and 20D are schematics of other slit jet arrays operative according to the invention in enabling increased particle recovery at much longer standoff distances. The drawings are not to scale. In these figures, some of the geometries of slit jets 201 arrayed around a central suction port 202 are illustrated. FIG. 20A demonstrates that the slit jet geometry may also encompass a slit width that is variable along the length of the slit.

Figure 21:
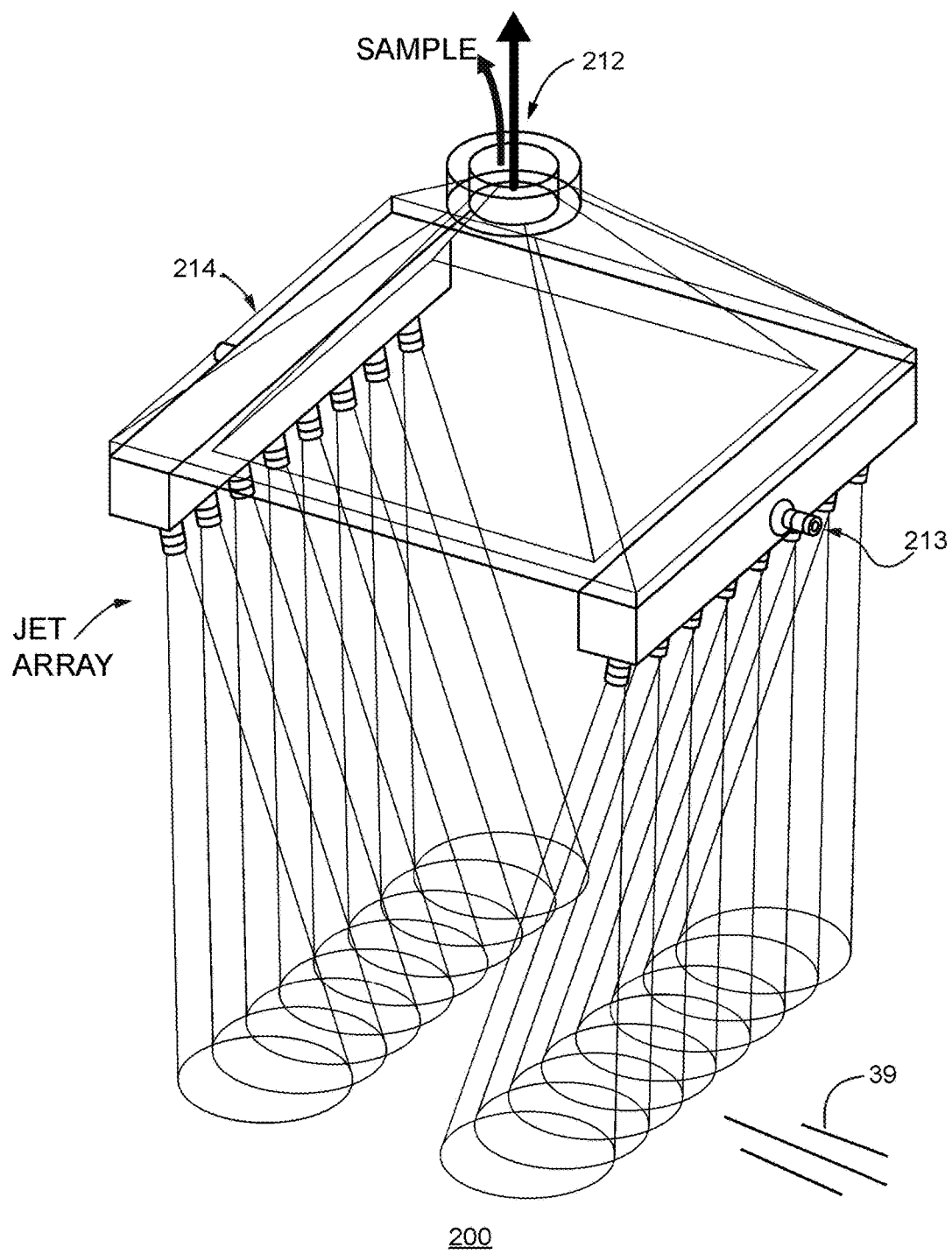

While pairs of slit jets are currently practiced, arrays of slit jet orifices or rounded nozzles are also contemplated. FIG. 21 is a perspective view of an apparatus 200 combining an array of two rows of tubular jet nozzles on either side of a central suction port 212. Diverging jet flow is indicated but the impaction zone is essentially a planar strip with a high aspect ratio. Air pressure at an inlet 213 is distributed into two jet manifolds 214 having each a row of jet nozzles directed angularly at a substrate surface 39. The rows of tubular jet nozzles are arrayed on either side of an elevated suction port where sample aerosol aspirate is collected for further concentration and analysis. In this configuration, overlaps are additive and the array behaves somewhat like a slit jet in the same sense that it has a high aspect ratio.

Figure 22A:
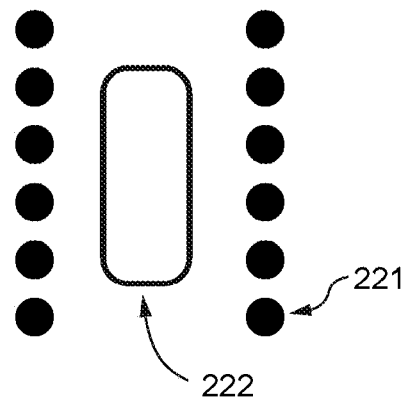
Figure 22B:
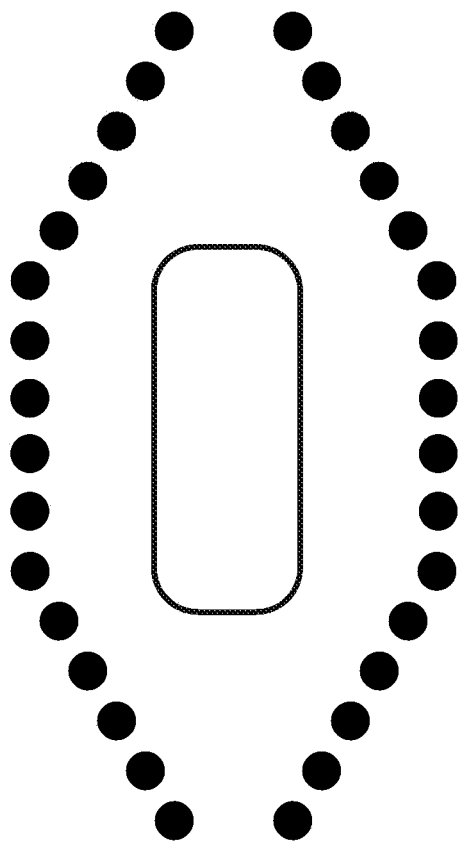

FIGS. 22A and 22B suggest that round jet arrays having an extended aspect ratio (>10) in linear segments also achieve a higher capture efficiency at greater standoff distances. Arrays of round jets 221 can be constructed around a suction port 222 in a variety of linear or bent linear row geometries that are expected to emulate the properties of slit jets.

FIG. 23 is a representative model of a process for operating a slit jet array of the invention. In a first step, a user is provided with a non-contacting sampler head and apparatus of the invention; paired planar jet bursts are used to generate opposing supersonic wall jets. The apparatus is supplied with a source of pressurized gas (commonly air) and a suction pressure source. The apparatus is actuated so that pulsatile flow of the pressurized gas through the jet orifices is initiated at the same time or after a suction pressure regime is established in the suction intake. The jets are characteristically planar jets having a high aspect ratio and are angled or steered so that impingement of the jets on a solid surface generates opposing wall jets that meet from opposite directions between the jet orifices and under the suction intake. Particles, including those having small aerodynamic dimensions, are mobilized and may be lifted off in the turbulent zone where the wall jets collide. Vapors and the boundary layer itself are carried with the rising return jets into the suction intake. This uplift efficiently collects target analytes and directs them into the suction intake port for further processing. Analysis and concentration modules for analyzing particles and vapors are known in the art and may be used in combination with the non-contacting sampler heads of the invention. The non-contacting sampler head may be moved along a surface so as to survey a large sampling area. Standoff distances of 12 inches or more are achieved at realizable pressures, an advance in the art. The needed pressures are in a range (typically less than 30 psig) such that portable, hand held non-contacting samplers are realized.

The method for aerodynamic liberation and capture of particles from a solid surface and vapors from any gaseous boundary layer may include a) first providing a non-contacting sampler apparatus having a sampler head bounded by a frame, the head comprising a central sampling intake port and pairs of slit jet orifices or arrays of slit jet orifices such that each pair of slit jet orifices is generally parallel and is separated by the sampling intake port; b) then coupling the sampling intake port to a suction pressure source and coupling the slit jet orifices or arrays to a gaseous fluid pressure reservoir and a jet pressure source such that each slit jet orifice is valvedly controlled by a high speed valve, each the pair having a first slit jet orifice configured to discharge a first planar jet and a second slit jet orifice configured to discharge a second planar jet toward a target surface, wherein the slit jet orifices or arrays have an aspect ratio of length to width configured to emit jet generally planar jet bursts, and further wherein the first planar jet and second planar jet are configured to converge at a virtual line behind a target surface; and c) actuating the sampling intake port by applying a suction pressure sufficient to draw the planar jet bursts into the sampling intake port; d) actuating release of planar jet bursts through each of the slit jet orifices or arrays, wherein the jets are configured to impinge on a solid surface at a standoff distance; and, e) concentrating or collecting any target analyte or analytes drawn into the sampling intake port.

It is desirable to periodically clean sand, ash and fibers from the suction port, and a piezoelectric crystal mounted on the cavity body facilitates this function. Actuation of the piezoelectric crystal impels sedimented material back into the bulk flow from which it is blown to exhaust.

Surprisingly, ultrasonic transducers applied to the bell or intake has little or no effect on the stability of the planar jet flow and sample uplift. Thus an ultrasonic cleaning function can be operated during sampling and under very dusty conditions, can be operated at regular periodicity during sampling without loss of analyte, a finding that would defy prediction given the large size of the intake bell.

A preferred system requires little maintenance and operates with a relative absence of moving parts such that the gas phase is the vehicle for both selectively separating and conveying vapors stripped from the particles to an analytical module. These and other analytical techniques are known in the art and may for example involve aerodynamic lenses or vortex samplers.

The device may be operated continuously or semi-continuously, unlike other impactors or other collection media (filters, adsorbent substrates, etc.) which must be periodically regenerated during use. Volatiles may be supplied to analysis by continuous in-line volatilization, unlike prior art applications having intermittent flash vaporization or off-line vaporization of replaceable cartridges or pledgets.

Example I

A non-contacting sampler body having axisymmetric slit jets arranged around a central suction cavity was fabricated. When operated so that planar slit jets are impacted on a solid surface, the model demonstrated a very high wall jet velocity and shock fronts using Schlieren photography (indicating the strength of the jet). The scaling factors are determined from parameters such as H/D and $P_{jet\ injector}/P_0$. Particle tracking technics were used to determine the flow structure location the linear jet. These visualization experiments validate the approach of using jet timing to attack sampling quality of uneven and tilted surfaces. Particle capture from a surface was demonstrated by high speed photography.

Surprisingly, shock trains in the wall jet were readily demonstrated with use of planar slit jets at moderate pressures. By opposing two wall jets, efficient particle capture was demonstrated for slit jets having aspect ratios greater than 10, more preferably greater than 50.

From these design considerations, the threshold values for particle removal can be achieved by the planar jet at longer stand-off distance/or lower operating pressures, exceeding expectations as experimentally shown. Serendipitously, the planar jet pairs also produce high forces much farther away from the impingement point, thereby extending the "reach" factor for the sample.

Example II

Portable devices made with planar jet arrays in the non-contacting sampler head were found to be operable, achieving superior results with less energy and without the use of compressed gas reservoirs. These devices were mounted on a robotic arm.

By a process of miniaturization, self-contained devices having dimensions and weight suitable as hand held sampling tools are realized.

INCORPORATION BY REFERENCE

All of the U.S. Patents, U.S. Patent application publications, U.S. Patent applications, foreign patents, foreign patent applications and non-patent publications referred to in this specification and related filings are incorporated herein by reference in their entirety for all purposes.

SCOPE OF THE CLAIMS

The disclosure set forth herein of certain exemplary embodiments, including all text, drawings, annotations, and graphs, is sufficient to enable one of ordinary skill in the art to practice the invention. Various alternatives, modifications and equivalents are possible, as will readily occur to those skilled in the art in practice of the invention. The inventions, examples, and embodiments described herein are not limited to particularly exemplified materials, methods, and/or structures and various changes may be made in the size, shape, type, number and arrangement of parts described herein. All embodiments, alternatives, modifications and equivalents may be combined to provide further embodiments of the present invention without departing from the true spirit and scope of the invention.

In general, in the following claims, the terms used in the written description should not be construed to limit the claims to specific embodiments described herein for illustration, but should be construed to include all possible embodiments, both specific and generic, along with the full scope of equivalents to which such claims are entitled. Accordingly, the claims are not limited in haec verba by the disclosure.

The embodiments of the figures and description were chosen and described in order to best explain the principles of the invention and its practical applications, to thereby enable others skilled in the art to best utilize the invention and various embodiments with various modifications as are suited to the particular use contemplated. However, it is intended that the scope of the invention be defined by the following claims, claim amendments, and their equivalents.

What is claimed is:

1. A method for aerodynamic liberation and capture of particles from a solid surface and vapors from any gaseous boundary layer, the method comprising:

a) providing a non-contact sampler apparatus having a sampler head bounded by a frame, the head comprising a central sampling intake port and a pair or pairs of slit jet orifices or arrays of slit jet orifices such that each pair of slit jet orifices is generally parallel and said sampling intake port is disposed between said pair or pairs of slit jet orifices;

b) coupling the sampling intake port to a suction pressure source and coupling the slit jet orifices or arrays to a pressure reservoir and a jet pressure source such that each slit jet orifice is valvedly controlled by a high speed valve, each said pair having a first slit jet orifice configured to discharge a first gaseous jet burst or bursts and a second slit jet orifice configured to discharge a second gaseous jet burst or bursts toward a target surface, wherein the slit jet orifices or arrays have an aspect ratio of length to width configured to emit generally planar jet bursts, and further wherein said first planar jet burst or bursts and second planar jet burst or bursts are configured to converge at a virtual line behind a target surface;

c) actuating the sampling intake port by applying a suction pressure sufficient to draw said planar jet bursts into said sampling intake port;

d) actuating release of a planar jet burst or bursts through each of the slit j et orifices or arrays, wherein the jets are configured to impinge on a target surface at a standoff distance; and, e) concentrating or collecting any target analyte or analytes drawn into the sampling intake port.

2. The method of claim 1, further comprising configuring each pair or pairs of slit jet orifices to emit each a planar jet burst, wherein said planar jet bursts impact a target surface at an angle and generate two wall jets in generally opposite directions such that said wall jets collide and rise up.

3. The method of claim 2, further comprising controlling said valves by a processor according to an executable instruction set stored in a non-transient memory.

4. The method of claim 3, further comprising configuring the processor to vary jet pulse duration, frequency and timing.

5. The method of claim 3, further comprising configuring the processor to emit a continuous series of paired pulses, wherein a first striking jet burst and a second-striking jet burst are distinguished by relative velocity or duration.

6. The method of claim 3, further comprising configuring the processor for operating valve timing allow for differences in surface contour between two points on the target surface upon which the jets strike.

7. The method of claim 3, further comprising configuring the processor for coordinating jet bursts so as to effect a sweeping and lifting action on particles and vapors dislodged from a substrate surface.

8. The method of claim 7, further comprising mapping a target surface and creating a three-dimensional map of a target surface, and then controlling jet burst timing according to said map.

9. The method of claim 7, further comprising operatively linking said processor to a range finder module and optimizing a valve timing waveform according to a three-dimensional map of a target surface.

10. The method of claim 7, further comprising controlling and adjusting planar jet burst parameters selected from: jet angle, jet burst timing, jet burst duration, jet velocity, pairwise jet-to-jet distance, jet aperture length, and standoff height according to a signal or signals received from a particle or vapor sensor mounted in said suction intake port, wherein said signal or signals are indicative of a target analyte or analytes drawn into the sampling intake port.

11. The method of claim 7, further comprising a user interface for controlling said sampler apparatus.

12. The method of claim 2, comprising mounting said sampler head on a tiltable arm or on a robotic arm.

13. The method of claim 1, further comprising providing the non-contact sampler apparatus with a handle for manual use and providing the suction pressure source and the jet pressure source in a compact portable form, further wherein said jet pressure source has a pressure greater than ambient when said valve is open.

14. The method of claim 13, comprising hand carrying said non-contact sampler and using a trigger for actuating the jet pressure and suction pressure sources, said non-contact sampler weighing less than ten pounds and having no external connections.

15. The method of claim 1, comprising providing a portal or gateway configured for passing a human, a parcel, or a suitcase between two or more of said non-contact sampler heads mounted in said portal or gateway.

\* \* \* \* \*